(12) United States Patent
Mihan et al.

(10) Patent No.: US 7,795,167 B2
(45) Date of Patent: Sep. 14, 2010

(54) CYCLOPENTADIENYL COMPLEXES OF GROUP 6 SUBSTITUTED BY SILYL HALIDES

(75) Inventors: Shahram Mihan, Bad Soden (DE); Markus Enders, Heidelberg (DE); Pablo Fernandez, Dublin (IE)

(73) Assignee: Basell Polyolefine GmbH, Wesseling (DE)

( * ) Notice: Subject to any disclaimer, the term of this patent is extended or adjusted under 35 U.S.C. 154(b) by 285 days.

(21) Appl. No.: 11/660,465

(22) PCT Filed: Aug. 16, 2005

(86) PCT No.: PCT/EP2005/008848

§ 371 (c)(1),
(2), (4) Date: Sep. 20, 2007

(87) PCT Pub. No.: WO2006/018264

PCT Pub. Date: Feb. 23, 2006

(65) Prior Publication Data

US 2008/0097053 A1    Apr. 24, 2008

Related U.S. Application Data

(60) Provisional application No. 60/622,958, filed on Oct. 27, 2004.

(30) Foreign Application Priority Data

Aug. 17, 2004    (DE) .................. 10 2004 039 877

(51) Int. Cl.
C08F 4/69       (2006.01)
C08F 4/6392     (2006.01)
B01J 31/22      (2006.01)
C07F 11/00      (2006.01)

(52) U.S. Cl. .................. 502/155; 502/103; 502/152; 502/167; 526/160; 526/161; 526/169; 526/172; 526/943; 556/58

(58) Field of Classification Search .................. 556/58; 502/152, 103, 155, 167; 526/160, 169, 943, 526/161, 172
See application file for complete search history.

(56) References Cited

U.S. PATENT DOCUMENTS

| | | | |
|---|---|---|---|
| 3,242,150 A | 3/1966 | Scoggin | |
| 3,248,179 A | 4/1966 | Norwood | |
| 3,709,853 A | 1/1973 | Karapinka | |
| 4,015,059 A | 3/1977 | Karol | |
| 4,361,497 A | 11/1982 | Boldt et al. | |
| 6,133,187 A * | 10/2000 | Vega et al. | 502/103 |
| 6,319,874 B1 | 11/2001 | Winter et al. | |
| 6,410,661 B1 | 6/2002 | Kaminsky et al. | |
| 6,417,302 B1 | 7/2002 | Bohnen | |
| 6,437,161 B1 | 8/2002 | Mihan et al. | |
| 6,589,905 B1 | 7/2003 | Fischer et al. | |
| 6,756,505 B1 | 6/2004 | Kristen et al. | |
| 6,784,261 B1 | 8/2004 | Schopf et al. | |
| 6,812,185 B2 | 11/2004 | Fischer et al. | |
| 6,881,493 B2 * | 4/2005 | Haveaux et al. | 428/523 |
| 7,053,160 B1 | 5/2006 | Bingel et al. | |
| 2003/0176275 A1 | 9/2003 | Fraaije et al. | |

FOREIGN PATENT DOCUMENTS

| | | |
|---|---|---|
| DE | 19710615 | 9/1998 |
| EP | 91/09882 | 7/1991 |
| WO | 97/04015 | 2/1997 |
| WO | 97/36937 | 10/1997 |
| WO | 98/22486 | 5/1998 |
| WO | 98/27124 | 6/1998 |
| WO | 98/40419 | 9/1998 |
| WO | 96/00243 | 1/1999 |
| WO | 99/06414 | 2/1999 |
| WO | 00/05277 | 2/2000 |
| WO | 00/24787 | 5/2000 |
| WO | 00/31090 | 6/2000 |
| WO | 00/35928 | 6/2000 |
| WO | 01/09148 | 2/2001 |
| WO | 01/41920 | 6/2001 |
| WO | 2004/020479 | 3/2004 |
| WO | 2004/056481 | 7/2004 |
| WO | 2004/056482 | 7/2004 |
| WO | 2004/106351 | 9/2004 |

OTHER PUBLICATIONS

Kirk-Othmer, Olefin Polymers (High Pressure Polyethylene), High Pressure (Low and Intermediate Density) Polyethylene; *Encyclopedia of Chemical Technology*, vol. 16, p. 402-420 (1981).

(Continued)

*Primary Examiner*—Caixia Lu
(74) *Attorney, Agent, or Firm*—Jarrod N. Raphael

(57) ABSTRACT

Cyclopentadienyl complexes of group 6 having at least one cyclopentadienyl system which is substituted by at least one silyl group which bears at least one halogen substituent and a catalyst system comprising at least one of the cyclopentadienyl complexes, and also a process for preparing them, the use of the catalyst system for the polymerization or copolymerization of olefins and a process for preparing polyolefins by polymerization or copolymerization of olefins in the presence of the catalyst system.

8 Claims, No Drawings

OTHER PUBLICATIONS

L. & M. Fieser, "Kapitel 33, Heterocyclen," *Lehrbuch der Organischen Chemie*, pp. 929-941 (1957).

Lettau, *Chemie der Heterocyclen*, 1st Edition, VEB, Weinheim, p. 17-27 (1979).

Ewen et al., "Expanding the Scope of Metallocene Catalysis: Beyond Indenyl and Fluorenyl Derivatives," *Springer Verlag*, p. 150-169 (1999).

R. Halterman, "Synthesis and Applications of Chiral Cyclopentadienylmetal Complexes," *Chem. Rev.*, p. 965-994 (1992).

S. Strauss, "The Search for Larger and More Weakly Coordinating Anions," *Chem. Rev.*, vol. 93(3), p. 927-942 (1993).

M. Enders et al., "Novel Reactivity of Ferrocene with Derivatives toward Lewis Acids: Decomplexation with Boron Trichloride and Synthesis of a Triple-Decker-like Iron-Zinc Complex," *Organometallics*, vol. 21(19), p. 3856-3859 (2002) XP-002374703.

M. Enders et al., "8-Quinolylcyclopentadienyl, a Ligand with a Tailored Fit for Chelate Complexes," *Chem. Ber.*, vol. 129, p. 459-463 (1996).

G. Britovsek et al., "Novel olefin polymerization catalysts based on iron and cobalt," *Chem. Commun.*, p. 849-850 (1998).

R. Dupont et al., "The Reaction of Arylacetones with Boron Tribomide," *Synthesis*, No. 9, p. 1651-1655 (1999) XP-002374705.

B. Small et al., "Highly Active Iron and Cobalt Catalysts for the Polymerization of Ethylene," *J. Am. Chem. Soc.*, vol. 120(16), p. 4049-4050 (1998).

R. Herrmann et al., "The Electrophilic Substitution of Ferrocene by Protonated Carbonyl Compounds," *Tetrahedron*, vol. 37(5), p. 1001-1009 (1981) XP-002374702.

W. Haubold et al., "Darstellung von Arylhalogenboranen," *Journal of Organometallic Chemistry*, vol. 315(1), p. 1-8 (1986) XP-002374706.

H. Wisenfeldt et al., "*ansa*-Metallocene derivatives. XVII. Racemic and *meso* diastereomers of group IV metallocene derivatives with symmetrically substituted, dimethylsilandiyl-bridged ligand frameworks. Crystal structure of R,S-Me$_2$Si(3-t-Bu-5-MeC$_5$H$_2$)$_2$ZrCl$_2$," *Journal of Organometallic Chemistry*, vol. 369, p. 359-370 (1989).

P. Jutzi et al., "Cyclopentadienyl compounds with nitrogen donors in the side-chain," *Journal of Organometallic Chemistry*, vol. 500, p. 175-185 (1995).

F. Javier de la Mata et al., "Synthesis and reactivity of new silyl-substituted monocyclopentadienyl molybdenum and tungsten complexes," *Journal of Organometallic Chemistry*, vol. 572(2), p. 155-161 (1999) XP-004152861.

T. Watanabe et al., "Selective and Stepwise Bromodemethylation of the Silyl Ligand in Iron (II) Silyl Complexes with Boron Tribomide," *Organometallics*, vol. 23(17), p. 4150-4153 (2004) XP-002374701.

E. Doyagüez, "Spotlight: Boron Tribromide," *Synlett*, No. 10, p. 1636-1637 (2005) XP-002374704.

J. Michl, Editor, *Chemical Reviews*, vol. 100(4), p, 1167-1681 (2000).

C. Narayana et al., "An efficient cleavage of lactones with boron triiodide-N, N-diethylaniline complex," *Tetrahedron Letters*, vol. 32(47), p. 6855-6856 (1991) XP-002374712.

G. Kabalka et al., "Boron triiodide-N, N-diethylaniline complex: a new reagent for cleaving esters," *Synthetic Communications*, vol. 22(12), p. 1793-8 (1992) XP-002374711.

W. Haubold et al., "Reaktionen von Bortrihalogeniden mit Tris-(trimethylsilyl)-amin," *Zeitschrift für Anorganische and Allgemeine Chemie*, vol. 421(2), p. 105-110 (1976) XP-002347407.

C. Narayana et al., "Cleavage of Ethers and Geminal Diacetates Using the Boron Triiodide-N, N-Diethylaniline Complex," *Tetrahedron Letters*, vol. 31(48), p. 6977-6978 (1990) XP-00168613.

C. Narayana et al., "Reductive Dimerization of Sulfonyl Derivatives to Disulfides and Deoxygenation of Sulfoxides to Sulfides Using the Boron Triiodide-N, N-Diethylaniline Comples," *Synlett*, No. 2, p. 125-126 (1991) XP-002374708.

S. Ciruelos et al., New Silyl-Substituted Cyclopentadienyl Titanium and Zirconium Complexes. X-ray Molecular Structures of [TiCl$_2$\{µ-(OSiMe$_2$-η$^5$-C$_5$H$_4$)\}]$_2$ and [ZrCl$_2$\{µ-[(η$^5$-C$_5$H$_4$)SiMe$_2$OSiMe$_2$(η$^5$-C$_5$H$_4$)]\}]; *Organometallics*, vol. 14, p. 177-185 (1995).

Doehring et al., "Donor-Ligand-Substituted Cyclopentadienylchromium(III) Complexes: A New Class of Alkene Polymerization Catalyst. 1. Amino-Substituted Systems"; *Organometallics*, vol. 19, No. 4, p. 388-402 (2000).

Ryan et al., "Gas-Phase Ionization Energetics, Electron-Transfer Kinetics, and Ion Solvation Thermochemistry of Decamethylmetallocenes, Chromocene, and Cobaltocene"; *Organometallics*, vol. 13, No. 4, p. 1190-1199 (1994).

* cited by examiner

CYCLOPENTADIENYL COMPLEXES OF GROUP 6 SUBSTITUTED BY SILYL HALIDES

The present invention relates to cyclopentadienyl complexes of group 6 having at least one cyclopentadienyl system which is substituted by at least one silyl group which bears at least one halogen substituent and to a catalyst system comprising at least one of the cyclopentadienyl complexes, and also to a process for preparing them.

In addition, the invention relates to the use of the cyclopentadienyl complex as intermediate, to the use of the catalyst system for the polymerization or copolymerization of olefins and to a process for preparing polyolefins by polymerization or copolymerization of olefins in the presence of the catalyst system.

Many of the catalysts which are used for the polymerization of $\alpha$-olefins are based on Immobilized chromium oxides (cf., for example, Kirk-Othmer, "Encyclopedia of Chemical Technology", 1981, Vol. 16, p. 402). These generally give ethylene homopolymers and copolymers having high molecular weights, but are relatively insensitive to hydrogen and thus do not allow simple control of the molecular weight. On the other hand, when bis(cyclopentadienyl)chromium (U.S. Pat. No. 3,709,853), bis(indenyl)chromium or bis(fluorenyl)chromium (U.S. Pat. No. 4,015,059) applied to an inorganic, oxidic support is used, the molecular weight of polyethylene can be controlled in a simple fashion by addition of hydrogen.

The functionalization of the cyclopentadienyl radicals of complexes of group 6 is not always easy. Functionalization with polar or reactive groups in particular often presents problems in the synthesis, since the cyclopentadienyl system is generally introduced as anion in the synthesis of the transition metal complexes. This anion reacts with reactive groups present or the reactive groups are attacked even sooner by the deprotonation reagent used for generating the anion.

We have now found a method by means of which silyl-substituted cyclopentadienyl complexes of group 6 are converted into cyclopentadienyl complexes substituted by silyl halides. This is a simple way of preparing functionalized cyclopentadienyl compounds of group 6, especially since the starting materials, viz. the sill-substituted cyclopentadienyl complexes of group 6, can be prepared in a simple fashion and in large quantities by reaction of silyl-substituted cyclopentadienyl anions with chromium compounds such as chromium trichloride.

The present invention provides cyclopentadienyl complexes of group 6 having at least one cyclopentadienyl system which is substituted by at least one silyl group which bears at least one halogen substituent and a catalyst system comprising at least one of the cyclopentadienyl complexes of group 6, and also a process for preparing them. Furthermore, the use of the cyclopentadienyl complexes of group 6 or of the catalyst system for the polymerization or copolymerization of olefins and a process for preparing polyolefins by polymerization or copolymerization of olefins in the presence of the cyclopentadienyl complexes of group 6 or of the catalyst system have been found.

The silyl group which bears a halogen substituent is preferably an $SiR^2D$ group, where D is fluorine, chlorine, bromine or iodine, in particular chlorine or bromine, the radicals R are each, independently of one another, hydrogen, $C_1$-$C_{22}$-alkyl, $C_2$-$C_{22}$alkenyl, $C_6$-$C_{22}$-aryl, arylalkyl having from 1 to 16 carbon atoms in the alkyl part and from 6 to 21 carbon atoms in the aryl part, $NR^1{}_2$, $N(SiR^1{}_3)_2$, $OR^1$, $OSiR^1{}_3$, $SiR^1{}_3$, where the organic radicals R may also be substituted by halogens and/or two radicals R may also be joined to form a five-, six- or seven-membered ring, and the radicals $R^1$ are each, independently of one another, hydrogen, $C_1$-$C_{22}$alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring.

The novel cyclopentadienyl complex of group 6 preferably bears at least one cyclopentadienyl radical having one or more substituents $SiR_2D$, preferably one substituent $SiR_2D$. A total of 1, 2 or 3 substituents $SiR_2D$ can be bound to the cyclopentadienyl radical. Preference is given to one substituent $SiR_{20}$ being bound to the cyclopentadienyl radical.

Preference is given to substituents $SiR_2D$ in which R is $C_1$-$C_{22}$-alkyl, $C_4$-$C_{22}$-alkenyl, $C_6$-$C_{22}$-aryl, arylalkyl having from 1 to 16 carbon atoms in the alkyl part and from 6 to 21 carbon atoms in the aryl part, with two radicals R also being able to be joined to form a five-, six- or seven-membered ring, in particular $C_1$-$C_{22}$-alkyl. D is preferably Cl or Br. The radicals R are particularly preferably selected from among methyl, ethyl, n-propyl, isopropyl, n-butyl, isobutyl, tert-butyl, n-pentyl, cyclopentyl, cyclohexyl, cycloheptyl, n-hexyl, n-heptyl, n-octyl, n-nonyl, n-decyl, phenyl, naphthyl, biphenyl, anthranyl, o-, m-, p-methylphenyl, 2,3-, 2,4-, 2,5-, 2,6-dimethylphenyl, 2,3,4-, 2,3,5-, 2,3,6-, 2,4,5-, 2,4,6- or 3,4,5-trimethylphenyl and benzyl.

Preference is given here to monocyclopentadienyl complexes of group 6 in which the cyclopentadienyl system is substituted by at least one bridged donor and at least one silyl group $SiR_2D$.

Preference is given to cyclopentadienyl complexes of group 6 comprising the following structural feature of the general formula $CpM^{1,4}$ (I), where the variables have the following meanings:

Cp is a cyclopentadienyl system having at least one $SiR_2D$ substituent,

D is fluorine, chlorine, bromine or iodine, in particular chlorine or bromine $M^{1,4}$ is chromium, molybdenum or tungsten, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1{}_2$, $N(SiR^1{}_3)_2$, $OR^1$, $OSiR^1{}_3$, $SiR^1{}_3$, where the organic radicals R may also be substituted by halogens and/or two radicals R may also be joined to form a five-, six- or seven-membered ring, and the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring.

Preference is given to complexes of the general formula (II)

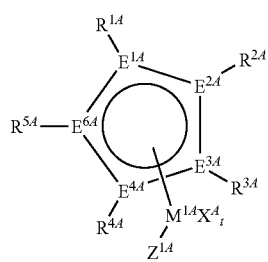

(II)

where the substituents and indices have the following meanings:

$M^{1A}$ is chromium, molybdenum or tungsten, $X^A$ is fluorine, chlorine, bromine, iodine, hydrogen, $C_1$-$C_{10}$-alkyl, $C_2$-$C_{10}$-alkenyl, $C_6$-$C_{22}$-aryl, arylalkyl having from 1 to 10 carbon atoms in the alkyl part and from 6 to 20 carbon atoms in the aryl part, —$OR^{6A}$ or —$NR^{6A}R^{7A}$, $SO_3R^{6A}$, $OC(O)R^{6A}$, CN, SCN, β-diketonate, CO, $BF_4^-$, $PF_6^-$ or bulky noncoordinating anions or two radicals $X^A$ for a substituted or unsubstituted diene ligand, in particular a 1,3-diene ligand, and the radicals $X^A$ are identical or different and may be bound to one another, or $X^A$ is a ligand of the following group:

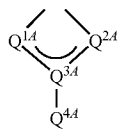

where
$Q^{1A}$-$Q^{2A}$ is O, $NR^{6A}$, $CR^{6A}R^{7A}$ or S, and $Q^{1A}$ and $Q^{2A}$ are bound to $M^{1A}$,
$Q^{3A}$ is C or S and
$Q^{4A}$ is $OR^{6A}$, $SR^{6A}$, $NR^{6A}R^{7A}$, $PR^{6A}R^{7A}$, hydrogen, $C_1$-$C_{10}$-alkyl, $C_2$-$C_{10}$-alkenyl, $C_6$-$C_{22}$-aryl, arylalkyl having from 1 to 10 carbon atoms in the alkyl part and from 6 to 20 carbon atoms in the aryl part or $SiR^{6A}_3$,
$E^{1A}$-$E^{5A}$ are each carbon or not more than one $E^{1A}$ to $E^{5A}$ is phosphorus or nitrogen, preferably carbon,
t is 1, 2 or 3 and is such that, depending on the valence of $M^{1A}$, the complex of the general formula (II) is uncharged, where
$R^{1A}$ to $R^{5A}$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^{8A}_2$, $N(SiR^{8A}_3)_2$, $OR^{8A}$, $OSiR^{8A}_3$, $SiR^{8A}_3$, where the organic radicals $R^{1A}$-$R^{5A}$ may also be substituted by halogens and/or two radicals $R^{1A}$-$R^{5A}$, in particular vicinal radicals, may also be joined to form a five-, six- or seven-membered ring and/or two vicinal radicals $R^{1A}$-$R^{5A}$ may be joined to form a five-, six- or seven-membered heterocycle which contains at least one atom from the group consisting of N, P, O and S, and at least one $R^{1A}$ to $R^{4A}$ is a substituent $SiR_2D$, where D is fluorine, chlorine, bromine or iodine, in particular chlorine or bromine, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1_2$, $N(SiR^1_3)_2$, $OR^1$, $OSiR^1_3$, $SiR^1_3$, where the organic radicals R may also be substituted by halogens and/or two radicals R may also be joined to form a five-, six- or seven-membered ring, the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring, $R^{6A}$ and $R^{7A}$ are each, independently of one another, $C_1$-$C_{10}$-alkyl, $C_2$-$C_{22}$-alkenyl, $C_6$-$C_{22}$-aryl, arylalkyl having from 1 to 10 carbon atoms in the alkyl part and from 6 to 20 carbon atoms in the aryl part, where the organic radicals $R^{6A}$ and $R^{7A}$ may also be substituted by halogens and/or two radicals $R^{6A}$ and $R^{7A}$ may also be joined to form a five-, six- or seven-membered ring, or $SiR^{8A}_3$ and the radicals $R^{8A}$ can be identical or different and can each be $C_1$-$C_{10}$-alkyl, $C_2$-$C_{22}$-alkenyl, $C_6$-$C_{22}$aryl, arylalkyl having from 1 to 10 carbon atoms in the alkyl part and from 6 to 20 carbon atoms in the aryl part, $C_1$-$C_{10}$-alkoxy or $C_6$-$C_{10}$-aryloxy, where the organic radicals $R^{8A}$ may also be substituted by halogens and/or two radicals $R^{8A}$ may also be joined to form a five-, six- or seven-membered ring, and $Z^{1A}$ is $X^A$ or

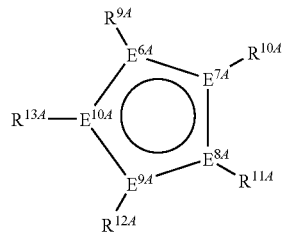

where the radicals
$R^{9A}$ to $R^{13A}$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and 6-21 carbon atoms in the aryl part, $R^{14A}$—C(O)O, $R^{14A}$—C(O)NR^{14A}$, $NR^{14A}_2$, $N(SiR^{14A}_3)_2$, $OR^{14A}$, $OSiR^{14A}_3$, $SiR^{14A}_3$, $SiR_2D$, where the organic radicals $R^{9A}$-$R^{13A}$ may also be substituted by halogens and/or two radicals $R^{9A}$-$R^{13A}$, in particular vicinal radicals, may also be joined to form a five-, six- or seven-membered ring and/or two vicinal radicals $R^{9A}$-$R^{13A}$ may be joined to form a five-, six- or seven-membered heterocycle which contains at least one atom from the group consisting of N, P, O and S, where the radicals $R^{14A}$ are identical or different and are each $C_1$-$C_{10}$-alkyl, $C_2$-$C_{22}$-alkenyl, $C_6$-$C_{22}$-aryl, arylalkyl having from 1 to 10 carbon atoms in the alkyl part and from 6 to 20 carbon atoms in the aryl part, $C_1$-$C_{10}$-alkoxy or $C_6$-$C_{10}$-aryloxy, where the organic radicals $R^{14A}$ may also be substituted by halogens and/or two radicals $R^{14A}$ may also be joined to form a five-, six- or seven-membered ring, and $E^{6A}$-$E^{10A}$ are each carbon or not more than one $E^{6A}$ to $E^{10A}$ is phosphorus or nitrogen, preferably carbon, or the radicals $R^{5A}$ and $Z^{1A}$ together form a —$R^{15A}_v$-$A^{1A}$ group in which $R^{15A}$

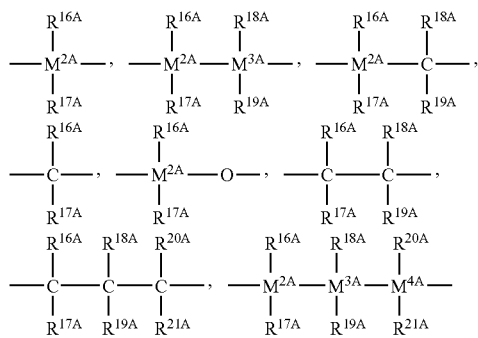

$=BR^{16A}$, $BNR^{16A}R^{17A}$, $AlR^{16A}$, —Ge—, —Sn—, —O—, —S—, $=SO$, $=SO_2$, $=NR^{16A}$, $=CO$, $=PR^{16A}$ or $=P(O)R^{16A}$, where $R^{16A}$-$R^{21A}$ are identical or different and are each a hydrogen atom, a halogen atom, $Si(R^{23A})_3$, $C_1$-$C_{10}$-alkyl, $C_2$-$C_{22}$-alkenyl, $C_6$-$C_{22}$-aryl, arylalkyl having from 1 to 10 carbon atoms in the alkyl part and from 6 to 20 carbon atoms in the aryl part, $C_1$-$C_{10}$-alkoxy or $C_6$-$C_{10}$-aryloxy, where the organic radicals $R^{16A}$-$R^{21A}$ may also be substituted by halogens and/or two radicals $R^{16A}$-$R^{21A}$ may also be joined to form a five-, six- or seven-membered ring, and $M^{2A}$-$M^{4A}$ are each silicon, germanium or tin, preferably silicon, $A^{1A}$

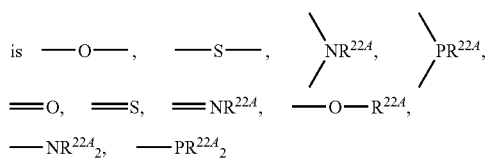

or an unsubstituted, substituted or fused, heterocyclic ring system, where the radicals $R^{22A}$ are each, independently of one another, $C_1$-$C_{10}$-alkyl, $C_2$-$C_{22}$-alkenyl, $C_6$-$C_{22}$-aryl, arylalkyl having from 1 to 10 carbon atoms in the alkyl part and from 6 to 20 carbon atoms in the aryl part or $Si(R^{23A})_3$, where the organic radicals $R^{22A}$ may also be substituted by halogens and/or two radicals $R^{22A}$ may also be joined to form a five-, six- or seven-membered ring, $R^{23A}$ is hydrogen, $C_1$-$C_{10}$-alkyl, $C_2$-$C_{22}$-alkenyl, $C_6$-$C_{22}$-aryl, arylalkyl having from 1 to 10 carbon atoms in the alkyl part and from 6 to 20 carbon atoms in the aryl part, where the organic radicals $R^{23A}$ may also be substituted by halogens and/or two radicals $R^{23A}$ may also be joined to form a five-, six- or seven-membered ring, v is 1 or when $A^{1A}$ is an unsubstituted, substituted or fused, heterocyclic ring system may also be 0, or the radicals $R^{5A}$ and $R^{13A}$ together form a —$R^{15A}$— group.

At least one radical $R^{1A}$ to $R^{4A}$ is a substituent $SiR_2D$. A total of 1, 2 or 3 radicals $R^{1A}$ to $R^{4A}$ can be a substituent $SiR_2D$. Preference is given to one radical $R^{1A}$ to $R^{4A}$ being a substituent $SiR_2D$.

Preference is given to substituents $SiR_2D$ in which R is $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where two radicals R may also be joined to form a five-, six- or seven-membered ring, in particular $C_1$-$C_{22}$-alkyl. D is preferably Cl or Br. The radicals R are particularly preferably selected from among methyl, ethyl, n-propyl, isopropyl, n-butyl, isobutyl, tert-butyl, n-pentyl, cyclopentyl, cyclohexyl, cycloheptyl, n-hexyl, n-heptyl, n-octyl, n-nonyl, n-decyl, phenyl, naphthyl, biphenyl, anthranyl, o-, m-, p-methylphenyl, 2,3-, 2,4-, 2,5-, 2,6-dimethylphenyl, 2,3,4-, 2,3,5-, 2,3,6-, 2,4,5-, 2,4,6- or 3,4,5-trimethylphenyl and benzyl.

For the purposes of the present invention, alkyl is a linear, branched or cyclic alkyl, e.g. methyl, ethyl, n-propyl, isopropyl, n-butyl, isobutyl, tert-butyl; n-pentyl, cyclopentyl, cyclohexyl, cycloheptyl, n-hexyl, n-heptyl, n-octyl, n-nonyl or n-decyl. Alkenyl is a linear, branched or cyclic alkenyl in which the double bond can be internal or terminal, e.g. vinyl, 1-allyl, 2-allyl, 3-allyl, 1-butenyl, 2-butenyl, 1-pentenyl, cyclopentenyl, cyclohexenyl or 1-hexenyl. $C_6$-$C_{22}$-aryl is an unsubstituted, substituted or fused aryl system in which the aryl radical may be substituted by further alkyl groups, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-; 2,3,6-, 2,4,5-, 2,4,6- or 3,4,5-trimethylphenyl. Arylalkyl is an aryl-substituted alkyl and may be substituted by further alkyl groups, e.g. benzyl, o-, m-, p-methylbenzyl, 1- or 2-ethylphenyl.

$A^{1A}$ together with the bridge $R^{15A}$ can, for example, form an amine, ether, thioether or phosphine. However, $A^{1A}$ may also be an unsubstituted, substituted or fused, heterocyclic aromatic ring system which can contain heteroatoms from the group consisting of oxygen, sulfur, nitrogen and phosphorus in addition to carbon ring atoms. Examples of 5-membered heteroaryl groups which may contain from one to four nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl and 1,2,4-triazol-3-yl. Examples of 6-membered heteroaryl groups which can contain from one to four nitrogen atoms and/or a phosphorus atom are 2-pyridinyl, 2-phosphaphenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

It is preferred that the radicals $X^A$ in the general formula (II) are identical, preferably fluorine, chlorine, bromine, $C_1$ to $C_7$-alkyl or aralkyl, in particular chlorine, methyl or benzyl.

This type of complexes of the formula (II) also includes compounds having at least one ligand which is formed by a cyclopentadienyl or heterocyclopentadienyl together with a fused-on heterocycle, with the heterocycles preferably being aromatic and preferably containing nitrogen and/or sulfur.

Particular preference is given to monocyclopentadienyl complexes comprising the following structural feature of the general formula Cp-Y$_m$M$^{1A}$ (III), where the variables have the following meanings:

Cp is a cyclopentadienyl system having at least one substituent SiR$_2$D, where

D is fluorine, chlorine, bromine or iodine, in particular chlorine or bromine, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, NR$^1_2$, N(SiR$^1_3$)$_2$, OR$^1$, OSiR$^1_3$, SiR$^1_3$, where the organic radicals R may also be substituted by halogens and/or two radicals R may also be joined to form a five-, six- or seven-membered ring, the radicals R$^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals R$^1$ may also be substituted by halogens and/or two radicals R$^1$ may also be joined to form a five-, six- or seven-membered ring, Y is a substituent which is bound to Cp and contains at least one uncharged donor, containing at least one atom of group 15 or 16 of the Periodic Table, M$^{1A}$ is chromium, molybdenum or tungsten and m is 1, 2 or 3.

The monocyclopentadienyl complexes of the invention comprise the structural element of the general formula Cp-Y$_m$M$^{1A}$ (III), where the variables are as defined above. Further ligands can consequently be bound to the metal atom M$^{1A}$. The number of further ligands depends, for example, on the oxidation state of the metal atom. The ligands are not further cyclopentadienyl systems. Suitable ligands are monoanionic and dianionic ligands as described by way of example for X. In addition, Lewis bases such as amines, ethers, ketones, aldehydes, esters, sulfides or phosphines may be bound to the metal center M$^{1A}$. The monocyclopentadienyl complexes can be monomeric, dimeric or oligomeric. The monocyclopentadienyl complexes are preferably in monomeric form.

M$^{1A}$ is a metal selected from the group consisting of chromium, molybdenum and tungsten. The oxidation state of the transition metals M$^{1A}$ in catalytically active complexes are usually known to those skilled in the art. Chromium, molybdenum and tungsten are very probably present in the oxidation state +3. However, it is also possible to use complexes whose oxidation state does not correspond to that of the active catalyst. Such complexes can then be appropriately reduced or oxidized by means of suitable activators. M$^{1A}$ is preferably chromium or molybdenum. Particular preference is given to chromium in the oxidation states 2, 3 and 4, in particular 3.

m can be 1, 2 or 3, i.e. 1, 2 or 3 donor groups Y can be bound to Cp. If 2 or 3 Y groups are present, these can be identical or different. Preference is given to only one donor group Y being bound to Cp (m=1).

The uncharged donor Y is an uncharged functional group containing an element of group 15 or 16 of the Periodic Table or a carbene, e.g. amine, imine, carboxamide, carboxylic ester, ketone, (oxo), ether, thioketone, phosphine, phosphite, phosphine oxide, sulfonyl, sulfonamide, carbenes such as N-substituted imidazol-2-ylidene or unsubstituted, substituted or fused, partially unsaturated heterocyclic or heteroaromatic ring systems. The donor Y can be bound intermolecularly or intramolecularly to the transition metal M$^{1A}$ or not be bound to it. Preference is given to the donor Y being bound intramolecularly to the metal center M$^{1A}$. Particular preference is given to the monocyclopentadienyl complexes comprising the structural element of the general formula

Cp is a cyclopentadienyl system which can bear any substituents and/or be fused with one or more aromatic, aliphatic, heterocyclic or heteroaromatic rings, with 1, 2 or 3 substituents, preferably 1 substituent, being formed by the group Y and/or 1, 2 or 3 substituents, preferably 1 substituent, being substituted by the group Y and/or the aromatic, aliphatic, heterocyclic or heteroaromatic fused ring bearing 1, 2 or 3 substituents Y, preferably 1 substituent Y. Furthermore, the cyclopentadienyl system bears one or more substituents SiR$_2$D, particularly preferably one substituent SiR$_2$D. The cyclopentadienyl skeleton itself is a C$_5$ ring system having 6 π-electrons, with one of the carbon atoms also being able to be replaced by nitrogen or phosphorus, preferably phosphorus. Preference is given to using C$_5$ ring systems which do not have a carbon atom replaced by a heteroatom. It is possible, for example, for a heteroaromatic containing at least one atom from the group consisting of N, P, O and S or an aromatic to be fused to this cyclopentadienyl skeleton. In this context, "fused to" means that the heterocycle and the cyclopentadienyl skeleton share two atoms, preferably carbon atoms. The cyclopentadienyl system is bound to M$^{1A}$.

Preferred embodiments of SiR$_2$D and the other variables are the same preferred embodiments, either alone or in combination, which have been mentioned above.

Particularly useful monocyclopentadienyl complexes are ones in which Y is formed by the group —R$^{15A}$-A$^{1A}$- and together with the cyclopentadienyl system Cp and M$^{1A}$ forms a monocyclopentadienyl complex comprising the structural element of the general formula Cp-R$^{15A}_v$-A$^{1A}$-M$^{1A}$ (IV), where the variables have the following meanings:

Cp-R$^{15A}_v$-A$^{1A}$ is

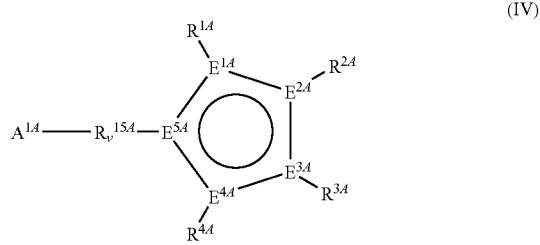

where the variables have the following meanings:

E$^{1A}$-E$^{5A}$ are each carbon or not more than one E$^{1A}$ to E$^{5A}$ is phosphorus, R$^{1A}$-R$^{4A}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl part and 6-20 carbon atoms in the aryl part, $NR^{8A}_2$, $N(SiR^{8A}_3)_2$, $OR^{8A}$, $OSiR^{8A}_3$, $SiR^{8A}_3$, $BR^{8A}_2$, where the organic radicals $R^{1A}$-$R^{4A}$ may also be substituted by halogens and two vicinal radicals $R^{1A}$-$R^{4A}$ may also be joined to form a five-, six- or seven-membered ring and/or two vicinal radicals $R^{1A}$-$R^{4A}$ are joined to form a five-, six- or seven-membered heterocycle which contains at least one atom from the group consisting of N, P, O and S and at least one $R^{1A}$-$R^{4A}$ is a substituent $SiR_2D$, D is fluorine, chlorine, bromine or iodine, in particular chlorine or bromine, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1_2$, $N(SiR^1_3)_2$, $OR^1$, $OSiR^1_3$, $SiR^1_3$, where the organic radicals R may also be substituted by halogens and/or two radicals R may also be joined to form a five-, six- or seven-membered ring, the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring, the radicals $R^{8A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two geminal radicals $R^{8A}$ may also be joined to form a five- or six-membered ring, $R^{15A}$ is a divalent bridge between $A^{1A}$ and Cp selected from the group consisting of

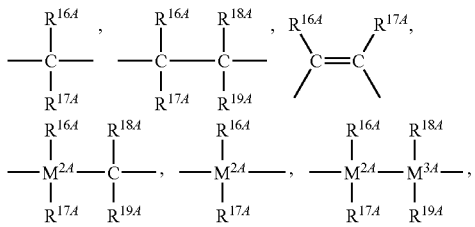

$M^{2A}$-$M^{3A}$ are each, independently of one another, silicon or germanium, $R^{16A}$-$R^{21A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{23A}_3$, where the organic radicals $R^{16A}$-$R^{21A}$ may also be substituted by halogens and two geminal or vicinal radicals $R^{16A}$-$R^{21A}$ may also be joined to form a five- or six-membered ring and the radicals $R^{23A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part, $C_1$-$C_{10}$-alkoxy or $C_6$-$C_{10}$-aryloxy and two radicals $R^{23A}$ may also be joined to form a five- or six-membered ring, and $A^{1A}$ is an uncharged donor group containing one or more atoms of group 15 and/or 16 of the Periodic Table of the Elements or a carbene, preferably an unsubstituted, substituted or fused, heteroaromatic ring system, $M^{1A}$ is a metal selected from the group consisting of chromium, molybdenum and tungsten and v is 0 or 1.

In preferred cyclopentadienyl systems Cp, all $E^{1A}$ to $E^{5A}$ are carbon.

The polymerization behavior of the metal complexes can be influenced by varying the substituents $R^{1A}$-$R^{4A}$. The type and number of the substituents can influence the ability of the olefins to be polymerized to gain access to the metal atom $M^{1A}$. It is possible in this way to modify the activity and selectivity of the catalyst in respect of various monomers, in particular bulky monomers. Since the substituents can also influence the rate of termination reactions of the growing polymer chain, the molecular weight of the polymers being formed can also be altered in this way. One of the substituents $R^{1A}$-$R^{4A}$ is always a $C_5$-$C_{22}$-aryl or an arylalkyl having from 1 to 10 carbon atoms in the alkyl part and 6-20 carbon atoms in the aryl part in order to achieve the desired results. The remaining substituents can be varied widely. Examples of possible carboorganic substituents $R^{1A}$-$R^{4A}$ are the following: hydrogen, $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent e.g. cyclopropane, cyclobutane, cyclopentane, cyclohexane, cycloheptane, cyclooctane, cyclononane or cyclododecane, $C_2$-$C_{22}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl and arylalkyl which may be substituted by further alkyl groups, e.g. benzyl, o-, m-, p-methylbenzyl, 1- or 2-ethylphenyl, where two of the radicals $R^{1A}$ to $R^{4A}$ may also be joined to form a 5-, 6- or 7-membered ring and/or two of the vicinal radicals $R^{1A}$-$R^{4A}$ may be joined to form a five-, six- or seven-membered heterocycle which contains at least one atom from the group consisting of N, P, O and S and/or the organic radicals $R^{1A}$-$R^{4A}$ may also be substituted by halogens such as fluorine, chlorine or bromine. Furthermore, $R^{1A}$-$R^{4A}$ can also be amino $NR^{8A}_2$, or $N(SiR^{8A}_3)_2$, alkoxy or aryloxy $OR^{8A}$, for example dimethylamino, N-pyrrolidinyl, picolinyl, methoxy, ethoxy or isopropoxy. In organosilicon substituents $SiR^{8A}_3$, the radicals $R^{8A}$ can be the same carboorganic radicals as described in more detail above for $R^{1A}$-$R^{4A}$, where two $R^{8A}$ may also be joined to form a 5- or 6-membered ring, e.g. trimethylsilyl, triethylsilyl, butyldimethylsilyl, tributylsilyl, tri-tert-butylsilyl, trialylsilyl, triphenylsilyl or dimethylphenylsilyl. These $SiR^{8A}_3$ radicals can also be bound to the cyclopentadienyl skeleton via oxygen or nitrogen, for example trimethylsilyloxy, triethylsilyloxy, butyldimethylsilyloxy, tributylsilyloxy or tri-tert-butylsilyloxy. Preferred radicals $R^{1A}$-$R^{4A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or -dichloro-substituted phenyls, trialkyl- or trichloro-substituted phenyls, naphthyl, biphenyl and anthranyl. Particularly useful organosilicon substituents are trialkylsilyl groups having from 1 to 10 carbon atoms in the alkyl radical, in particular trimethylsilyl groups.

Two vicinal radicals $R^{1A}$-$R^{4A}$ together with the atoms $E^{1A}$-$E^{5A}$ bearing them can form a heterocycle, preferably a heteroaromatic, which contains at least one atom from the group consisting of nitrogen, phosphorus, oxygen and sulfur, particularly preferably nitrogen and/or sulfur, with preference being given to the atoms $E^{1A}$-$E^{5A}$ present in the heterocycle or heteroaromatic being carbon. Preference is given to heterocycles and heteroaromatics having a ring size of 5 or 6 ring atoms. Examples of 5-membered heterocycles which can contain from one to four nitrogen atoms and/or a sulfur or oxygen atom as ring atoms in addition to carbon atoms are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole and 1,2,4-triazole. Examples of 6-membered heteroaryl groups which may contain from one to four nitrogen atoms and/or a phosphorus atom are pyridine, phosphabenzene, pyridazine, pyrimidine, pyrazine, 1,3,5-triazine, 1,2,4-triazine and 1,2,3-triazine. The 5-membered and 6-membered heterocycles can also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine, dialkylamide, arylalkylamide, diarylamide, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chromane, benzopyran, quinoline, isoquinoline, cinnoline, phthalazine, quinazoline, quinoxaline, 1,10-phenanthroline and quinolizine. Naming and numbering of the heterocycles has been taken from Lettau, Chemie der Heterocyclen, 1st edition, VEB, Weinheim 1979. The heterocycles/heteroaromatics are preferably fused with the cyclopentadienyl skeleton via a C—C double bond of the heterocycle/heteroaromatic. Heterocycles/heteroaromatics having one heteroatom are preferably 2,3- or b-fused.

Cyclopentadienyl systems Cp having a fused heterocycle are, for example, thiapentalene, methylthiapentalene, ethylthiapentalene, isopropylthiapentalene, n-butylthiapentalene, tert-butylthiapentalene, trimethylsilylthiapentalene, phenylthiapentalene, naphthylthiapentalene, methylthiapentalene, azapentalene, methylazapentalene, ethylazapentalene, isopropylazapentalene, n-butylazapentalene, trimethylsilylazapentalene, phenylazapentalene, naphthylazapentalene, oxapentalene or phosphapentalene.

The synthesis of such cyclopentadienyl systems having a fused-on heterocycle is described, for example, in the above-mentioned WO 98/22486. "Metalorganic catalysts for synthesis and polymerisation", Springer Verlag 1999, Ewen et al., p. 150 ff, describes further syntheses of these cyclopentadienyl systems.

Particularly preferred substituents $R^{1A}$-$R^{4A}$ are the above-described carboorganic substituents and the carboorganic substituents which form a cyclic fused ring system, i.e. together with the $E^{1A}$-$E^{5A}$ skeleton, preferably together with a CB-cyclopentadienyl skeleton, form, for example, an unsubstituted or substituted indenyl, benzindenyl, phenanthrenyl or tetrahydroindenyl system, and in particular their preferred embodiments.

Examples of such cyclopentadienyl systems (without the group —$R^{15A}_v$-$A^{1A}$-, which is preferably located in the 1 position, and without the aryl substituents) are monoalkylcyclopentadienyl systems, e.g. 3-methylcyclopentadienyl, 3-ethylcyclopentadienyl, 3-isopropylcyclopentadienyl, 3-tert-butylcyclopentadienyl, dialkylcyclopentadienyl systems, e.g. tetrahydroindenyl, 2,4-dimethylcyclopentadienyl and 3-methyl-5-tert-butylcyclopentadienyl, and trialkylcyclopentadienyl systems, e.g. 2,3,5-trimethylcyclopentadienyl, and also indenyl and benzindenyl. The fused ring system may bear further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part, $NR^{8A}_2$, $N(SiR^{8A}_3)_2$, $OR^{8A}$, $OSiR^{8A}_3$ or $SiR^{8A}_3$, e.g. 4-methylindenyl, 4-ethylindenyl, 4-isopropylindenyl, 5-methylindenyl, 4-phenylindenyl, 5-methyl-4-phenylindenyl or 4-naphthylindenyl.

At least one of the substituents $R^{1A}$-$R^{4A}$, preferably one substituent $R^{1A}$-$R^{4A}$, is a substituent $SiR_2D$. The preferred embodiments of $SiR_2D$ have been described above. The substituent $SiR_2D$ can be located in the vicinal position relative to the substituent —$R^{15A}_v$-$A^{1A}$ or the two substituents are located in the 1,3 positions relative to one another on the cyclopentadienyl ring. Preference is given to —$R^{15A}_v$-$A^{1A}$ and the substituent $SiR_2D$ being located in the 1,2 positions relative to one another on the cyclopentadienyl ring.

As in the case of the metallocenes, the monocyclopentadienyl complexes of the invention can be chiral. Thus, either-one of the substituents $R^{1A}$-$R^{4A}$ of the cyclopentadienyl skeleton can have one or more chiral centers or else the cyclopentadienyl system Cp can itself be enantiotopic, so that the chirality is induced only when it is bound to the transition metal $M^{1A}$ (for the conventions regarding chirality in cyclopentadienyl compounds, see R. Halterman, Chem. Rev. 92, (1992), 965-994).

The bridge $R^{15A}$ between the cyclopentadienyl system Cp and the uncharged donor $A^{1A}$ is an organic divalent bridge (v=1), preferably consisting of carbon- and/or silicon-containing bridge members. Changing the length of the link between the cyclopentadienyl system and $A^{1A}$ enables the activity of the catalyst to be influenced.

Possible carboorganic substituents $R^{16A}$-$R^{21A}$ on the link $R^{15A}$ are, for example, the following: hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropane; cyclobutane, cyclopentane, cyclohexane, cycloheptane, cyclooctane, cyclononane or cyclododecane, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4,2,5- or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals R to R may also be joined to form a 5- or 6-membered ring, for example cyclohexane, and the organic radicals $R^{16A}$-$R^{21A}$ may also be substituted by halogens, such as fluorine, chlorine or bromine, for example pentafluorophenyl or bis-3,5-trifluoromethylphen-1-yl, and alkyl or aryl.

In organosilicon substituents $SiR^{23A}_3$, possible radicals $R^{23A}$ are the same radicals mentioned in more detail above for $R^{16A}$-$R^{21A}$, where two $R^{23A}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. Preferred radicals $R^{23A}$ are methyl, ethyl, n-propyl, isopropyl, n-butyl, isobutyl, tert-butyl, n-pentyl, n-hexyl, n-heptyl, n-octyl, benzyl, phenyl, ortho-dialkyl- or dichloro-substituted phenyls, trialkyl- or trichloro-substituted phenyls, naphthyl, biphenyl and anthranyl.

Particularly preferred substituents $R^{16A}$ to $R^{21A}$ are hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two $R^{16A}$ to $R^{21A}$ may also be joined to form a 5- or 6-membered ring, for example cyclohexane, and the organic radicals $R^{16A}$-$R^{21A}$ may also be substituted by halogens such as fluorine, chlorine or bromine, in particular fluorine, for example pentafluorophenyl or bis-3,5-trifluoromethylphen-1-yl, and alkyl or aryl. Particular preference is given to methyl, ethyl, 1-propyl, 2-isopropyl, 1-butyl, 2-tert-butyl, phenyl and pentafluorophenyl.

$R^{15A}$ is preferably a —$CR^{16A}R^{17A}$—, —$SiR^{16A}R^{17A}$— group, in particular —$Si(CH_3)_2$—, —$CR^{16A}R^{17A}CR^{18A}R^{19A}$—, —$SiR^{16A}R^{17A}CR^{18A}R^{19A}$— or substituted or unsubstituted 1,2-phenylene and in particular —$CR^{16A}R^{17A}$—. Here, the preferred embodiments of the substituents $R^{16A}$ to $R^{21A}$ described above are likewise preferred embodiments. —$CR^{16A}R^{17A}$— is preferably a —$CHR^{16A}$—, —$CH_2$— or —$C(CH_3)_2$— group. The group —$SiR^{16A}R^{17A}$— in -$M^{2A}R^{16A}R^{17A}CR^{18A}R^{19A}$— can be bound to the cyclopentadienyl system or to $A^{1A}$. This group —$SiR^{16A}R^{17A}$— or its preferred embodiments is preferably bound to Cp.

v is 0 or 1, and is in particular equal to 1 or when $A^{1A}$ is an unsubstituted, substituted or fused, heterocyclic ring system can also be 0.

$A^{1A}$ is an uncharged donor containing an atom of group 15 or 16 of the Periodic Table or a carbene, preferably one or more atoms selected from the group consisting of oxygen, sulfur, nitrogen and phosphorus, preferably nitrogen or phosphorus. The donor function in $A^{1A}$ can be bound intermolecularly or intramolecularly to the metal $M^{1A}$. The donor in $A^{1A}$ is preferably bound intramolecularly to $M^{1A}$. Possible donors are uncharged functional groups containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, heterocyclic ring systems. The synthesis of the bond from $A^{1A}$ to the cyclopentadienyl radical and $R^{15A}$ can be carried out, for example, by a method analogous to that of WO 00/35928. $A^{1A}$ is preferably a group selected from among —$OR^{22A}$, —$SR^{22A}$, —$NR^{22A}_2$, —$PR^{22A}_2$, —$C\!=\!NR^{22A}$— and unsubstituted, substituted or fused heteroaromatic ring systems, in particular —$NR^{22A}_2$, —$C\!=\!NR^{22A}$— and unsubstituted, substituted or fused heteroaromatic ring systems.

The radicals $R^{22A}$ are, independently of one another, hydrogen, $C_1$-$C_{20}$-alkyl which may be linear, cyclic or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, cycloalkyl which may in turn bear a $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4, 5-, 2,4,6- or 3,4,5-trimethylphen-1-yl, arylalkyl which has from 1 to 10 carbon atoms in the alkyl part and 6-20 carbon atoms in the aryl part and may be substituted by further alkyl groups, e.g. benzyl, o-, m-, p-methylbenzyl, 1- or 2-ethylphenyl, or $SiR^{23A}_3$, where the organic radicals $R^{22A}$ may also be substituted by halogens such as fluorine, chlorine or bromine or nitrogen-containing groups and further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{23A}_3$ groups and two vicinal radicals $R^{22A}$ may also be joined to form a five- or six-membered ring and the radicals $R^{23A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{23A}$ may also be joined to form a five- or six-membered ring.

$NR^{22A}_2$ is an amide substituent. It is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tert-octyl-amide, dioctylamide, bis(2-ethylhexyl) amide, didecylamide, N-methyloctadecylamide, N-methylcyclohexylamide, N-ethylcyclohexylamide, N-isopropylcyclohexylamide, N-tert-butylcyclohexylamide, dicyclohexylamide, pyrrolidine, piperidine, hexamethylenimine, decahydroquinoline, diphenylamine, N-methylanilide or N-ethylanilide.

In the imino group —$C\!=\!NR^{22A}$, $R^{22A}$ is preferably a $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4,5-, 2,4,6- or 3,4,5-trimethylphen-1-yl.

$A^{1A}$ is preferably an unsubstituted, substituted or fused heteroaromatic ring system which may contain, apart from carbon ring atoms, heteroatoms from the group consisting of oxygen, sulfur, nitrogen and phosphorus. Examples of 5-membered heteroaryl groups which may, in addition to carbon atoms, contain from one to four nitrogen atoms or from one to three nitrogen atoms and/or one sulfur or oxygen atom as ring atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which may contain from one to four nitrogen atoms and/or a phosphorus atom are 2-pyridinyl, 2-phosphaphenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl or 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

Among these heteroaromatic systems $A^{1A}$, particular preference is given to unsubstituted, substituted and/or fused six-membered heteroaromatics having 1, 2, 3, 4 or 5 nitrogen atoms in the heteroaromatic part, in particular substituted and unsubstituted 2-pyridyl, 2-quinolyl or 8-quinolyl.

$A^{1A}$ is therefore preferably a group of the formula (Va) or (Vb)

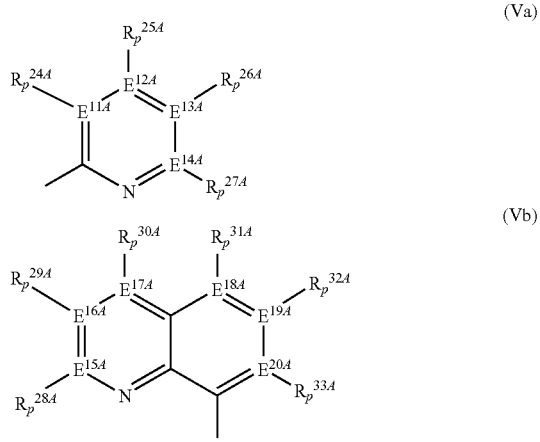

where
$E^{11A}$-$E^{20A}$ are each, independently of one another, carbon or nitrogen,
$R^{24A}$-$R^{33A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{34A}_3$, where the organic radicals $R^{24A}$-$R^{33A}$ may also be substituted by halogens or nitrogen and further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{34A}_3$ groups and two vicinal radicals $R^{24A}$-$R^{33A}$ or $R^{24A}$ and $R^{15A}$ may also be joined to form a five- or six-membered ring and
the radicals $R^{34A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{34A}$ may also be joined to form a five- or six-membered ring and
p is 0 when $E^{11A}$-$E^{20A}$ is nitrogen and is 1 when $E^{11A}$-$E^{20A}$ is carbon.

In particular, 0 or 1 of $E^{11A}$-$E^{20A}$ is nitrogen and the remainder are carbon. $A^{1A}$ is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

Owing to the ease of preparation, a preferred combination of $R^{15A}$ and $A^{1A}$ is when $R^{15A}$ is an unsubstituted or substituted 1,2-phenylene group and $A^{1A}$ is $NR^{22A}_2$, and also the combination in which $R^{15A}$ is —$CHR^{16A}$—, —$CH_2$—, —$C(CH_3)_2$ or —$Si(CH_3)_2$— and $A^{1A}$ is an unsubstituted or substituted 2-quinolyl or unsubstituted or substituted 2-pyridyl. Systems which do not have a bridge $R^{15A}$ and in which v is 0 are also particularly simple to obtain. In this case, $A^{1A}$ is preferably a substituent of the formula (Vb) and in particular unsubstituted or substituted 8-quinolyl. The above-described preferred embodiments of the variables are also preferred in these preferred combinations.

$M^{1A}$ is a metal selected from the group consisting of chromium, molybdenum and tungsten, preferably chromium. Particular preference is given to chromium in the oxidation states 2, 3 and 4, in particular 3.

Among the suitable monocyclopentadienyl complexes, preference is given to those of the general formula $Cp$-$Y_m M^{1A} X^A_n$ (VI), where the variables Cp, Y, m and $M^{1A}$ are as defined above and their preferred embodiments are also preferred here and:
the radicals $X^A$ are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, arylalkyl having from 1-10 carbon atoms in the alkyl part and 6-20 carbon atoms in the aryl part, $NR^{6A}R^{7A}$, $OR^{6A}$, $SR^{7A}$, $SO_3R^{6A}$, $OC(O)R^{7A}$, CN, SCN, β-diketonate, GO, $BF_4^-$, $PF_6^-$ or bulky noncoordinating anions or two radicals $X^A$ form a substituted or unsubstituted diene ligand, in particular a 1,3-diene ligand, and the radicals $X^A$ may be joined to one another,
$R^{6A}$-$R^{7A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part, $SiR^{6A}_3$, where the organic radicals $R^{6A}$-$R^{7A}$ may also be substituted by halogens or nitrogen- or oxygen-containing groups and two radicals $R^{6A}$-$R^{7A}$ may also be joined to form a five- or six-membered ring,
the radicals $R^{8A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two radicals $R^{8A}$ may also be joined to form a five- or six-membered ring and,
n is 1, 2, or 3.

The embodiments and preferred embodiments of Cp, Y, $R^{15A}$, $A^{1A}$, m, k and $M^{1A}$ indicated above also apply individually and in combination to these preferred monocyclopentadienyl complexes.

The ligands $X^A$ result from, for example, the choice of the metal compounds used as starting materials for the synthesis of the monocyclopentadienyl complexes, but can also be varied subsequently. Possible ligands $X^A$ are, in particular, the halogens, such as fluorine, chlorine, bromine or iodine, in particular chlorine. Alkyl radicals such as methyl, ethyl, propyl, butyl, vinyl, allyl, phenyl or benzyl are also advantageously ligands $X^A$. As further ligands $X^A$, mention may be made, purely by way of example and in no way exhaustively, of trifluoroacetate, $BF_4^-$, $PF_6^-$ and weakly coordinating or noncoordinating anions (cf., for example, S. Strauss in Chem. Rev. 1993, 93, 927-942) such as $B(C_6F_5)_4^-$.

Amides, alkoxides, sulfonates, carboxylates and β-diketonates are also particularly suitable ligands $X^A$. Variation of the radicals $R^{6A}$ and $R^{7A}$ makes it possible, for example, to make fine adjustments in physical properties such as solubility. Possible carboorganic substituents $R^{6A}$-$R^{7A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 3- to 12-membered cycloalkyl which may in turn bear a $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, or arylalkyl which may be substituted by further alkyl groups, e.g. benzyl, o-, m-, p-methylbenzyl, 1- or 2-ethylphenyl, where $R^{6A}$ may also be joined to $R^{7A}$ to form a 5- or 6-membered ring and the organic radicals $R^{6A}$-$R^{7A}$ may also be substituted by halogens such as fluorine, chlorine or bromine. In organosilicon substituents $SiR^{8A}_3$, the radicals $R^{8A}$ can be the same radicals described in more detail above for $R^{6A}$-$R^{7A}$, where two radicals $R^8$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl, and also vinyl, allyl, benzyl and phenyl as radicals $R^{6A}$ and $R^{7A}$. Some of these substituted ligands $X^A$ are particularly preferably used because they are obtainable from cheap and readily available starting materials. Thus, a particularly preferred embodiment is that in which $X^A$ is dimethylamide, methoxide, ethoxide, isopropoxide, phenoxide, naphthoxide, triflate, p-toluenesulfonate, acetate or acetylacetonate.

The number n of the ligands $X^A$ depends on the oxidation state of the transition metal $M^{1A}$. The number n can therefore not be given in general terms. The oxidation state of the transition metals $M^{1A}$ in catalytically active complexes is usually known to those skilled in the art. Chromium, molybdenum and tungsten are very probably present in the oxidation state+3. However, it is also possible to use complexes whose oxidation state does not correspond to that of the active catalyst. Such complexes can then be appropriately reduced or oxidized by means of suitable activators. Preference is given to using chromium complexes in the oxidation state+3.

Preferred monocyclopentadienyl complexes A) of this type are 1-(8-quinolyl)-3-(bromodimethylsilyl)cyclopentadienylchromium(III) dichloride, 1-(8-quinolyl)-3-(chlorodimethylsilyl)cyclopentadienylchromium(III) dichloride, 1-(8-quinolyl)-2-methyl-4-(bromodimethylsilyl)cyclopentadienylchromium(III) dichloride, 1-(8-quinolyl)-3-methyl-4-(bromodimethylsilyl)cyclopentadienylchromium(III) dichloride, 1-(8-quinolyl)-3-methyl-4-(chlorodimethylsilyl)cyclopentadienylchromium(III) dichloride, 1-(8-quinolyl)-2-methyl-4-(chlorodimethylsilyl)cyclopentadienylchromium(III) dichloride, 1-(8-quinolyl)-3-(bromodiethylsilyl)indenylchromium(III) dichloride, 1-(8-quinolyl)-3-(chlorodimethylsilyl)benzindenylchromium(III) dichloride, 1-(8-(2-methylquinolyl))-2-methyl-3-(bromodimethylsilyl)cyclopentadienylchromium(III) dichloride, 1-(8-(2-methylquinolyl))-3-(bromodimethyosilyl)indenyl-chromium(III) dichloride, 1-(2-pyridylmethyl)-3-(bromodimethylsily)cyclopentadienylchromium(III)dichloride, 1-(2-pyridylmethyl)-2-methyl-4-(chlorodimethylsilyl)cyclopentadienylchromium(III) dichloride, 1-(2-pyridylethyl)-3-(bromodimethylsilyl)cyclopentadienylchromium dichloride, 1-(2-pyridyl-1-methylethyl)-3-(chlorodimethylsilyl)phenylcyclopentadienylchromium dichloride or 1-(2-pyridyl-1-phenylmethyl)-3-(bromodimethylsilyl)cyclopentadienylchromium dichloride.

Furthermore, we have found a process for preparing cyclopentadienyl complexes of group 6 having at least one cyclopentadienyl system which bears at least one silyl group $SiR^2$, where D is fluorine, chlorine, bromine or iodine, in particular chlorine or bromine, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1_2$, $N(SiR^1_3)_2$, $OR^1$, $OSiR^1_3$, $SiR^1_3$, where the organic radicals R may also be substituted by halogens and/or two radicals R may also be joined to form a five-, six- or seven-membered ring, and the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring, which comprises reacting a cyclopentadienyl complex of group 6 having at least one cyclopentadienyl system which is substituted by at least one silyl group $SiR_3$ with $BD_3$.

$BD_3$ is a boron trihalide in which D is F, Cl, Br or I, and it can be used as a pure substance or in the form of a solution. The addition of the boron trihalides usually results in not only the R substituents of the alkyl group but often also the non-Cp ligands on $M^{1A}$ being substituted by D. If the cyclopentadienyl complex of group 6 having at least one substituent $SiR_3$ which is used is a bromide, dibromide or has no further ligands apart from Cp, then $BD_3$ is preferably used in a molar ratio of B:$SiR^3$ of from 0.4:1 to 100:1, preferably from 1:1 to 20:1. If further ligands $X^A$ which are not Br or Cp are coordinated to $M^{1A}$, then it is advantageous to use a further 0.4 to 10, preferably from 1 to 1.5 molar equivalents of $BD_3$ per $X^A$.

The preferred novel cyclopentadienyl complexes of group 6 having at least one substituent $SiR_2D$ are preferably prepared from the corresponding cyclopentadienyl complexes of group 6 having a substituent $SiR_3$. Preference is given to substituents $SiR_2D$ and $SiR_3$ in which R is $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, with two radicals R also being able to be joined to form a five-, six- or seven-membered ring, and is in particular $C_1$-$C_{22}$-alkyl. Alkyl groups on the silyl group $SiR_3$ can be replaced particularly easily but are easy to obtain synthetically. D is preferably Cl or Br. The radicals R are particularly preferably selected from among methyl, ethyl, n-propyl, isopropyl, n-butyl, isobutyl, tert-butyl, n-pentyl, cyclopentyl, cyclohexyl, cycloheptyl, n-hexyl, n-heptyl, n-octyl, n-nonyl or n-decyl.

As solvents, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene, or halogenated hydrocarbons such as carbon tetrachloride, chloroform or dichloromethane and mixtures thereof. The reactions can be carried out at temperatures of from −100 to +160° C., in particular from −80 to 100° C.

The cyclopentadienyl complexes of group 6, in particular the chromium complexes, having at least one silyl substituent $SiR_3$ can be obtained in a simple manner by reacting the appropriate metal salts, e.g. metal chlorides, with the appropriate $SiR_3$-substituted ligand anion (e.g. using a method analogous to the examples in DE 197 10615).

Preference is given to a process for preparing cyclopentadienyl complexes of group 6 comprising the following structural feature of the general formula $CpM^{14}$ (I), where the variables have the following meanings:

Cp is a cyclopentadienyl system having at least one $SiR_2D$ substituent,

D is fluorine, chlorine, bromine or iodine, in particular chlorine or bromine $M^{14}$ is chromium, molybdenum or tungsten, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1_2$, $N(SiR^1_3)_2$, $OR^1$, $OSiR^1_3$, $SiR^1_3$, where the organic radicals R may also be substituted by halogens and/or two radicals R may also be joined to form a five-, six- or seven-membered ring, and the radicals $R^1$ are each, independently of one another, hydrogen, $C_1$-$C_2$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring, which comprises reacting cyclopentadienyl complexes of group 6 comprising the following structural feature of the general formula $CpM^{14}$ (VI), where the variables have the following meanings:

Cp is a cyclopentadienyl system having at least one $SiR_3$ substituent, $M^{14}$ is chromium, molybdenum or tungsten, the radicals R are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^1_2$, $N(SiR^1_3)_2$, $OR^1$, $OSiR^1_3$, $SiR^1_3$, where the organic radicals R may also be substituted by halogens and/or two radicals R may also be joined to form a five-, six- or seven-membered ring, and the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 16 carbon atoms in the alkyl part and from 6 to 21 carbon atoms in the aryl part, where the organic radicals $R^1$ may also be substituted by halogens and/or two radicals $R^1$ may also be joined to form a five-, six- or seven-membered ring, with $BD_3$.

The preferred novel cyclopentadienyl complexes of group 6 having the formula II, III or IV and their preferred embodiments are preferably prepared in the process from the corresponding complexes in which $SiR_3$ is present in place of $SiR_2D$. Here, complexes in which $X^4$ is identical to D are preferably obtained.

The novel cyclopentadienyl complexes of group 6 obtained this way can be used to fix the $SiR_2D$ group to, for example, a support or as intermediates in the synthesis of further complexes, since the group D can easily be replaced. Thus, the cyclopentadienyl complexes of group 6 can be used to produce two different complexes in situ by adding one or more nucleophilic addition reagents such as alkali metal compounds, alkaline earth metal compounds or alkyl and/or aryl compounds of group 13, as mentioned below for E). In particular, cyclopentadienyl complexes of group 6 having a group $SiR_3$ in which at least one R is different from the other two can be prepared by this means. It is thus possible, for example, to produce bimodal polyolefin mixtures, in particular bimodal polyethylene mixtures, which can be regulated in situ by controlling the product by control of the addition of the reagent E).

The novel cyclopentadienyl complexes of group 6 can be used alone or together with further components as catalyst system for olefin polymerization. We have also found catalyst systems for olefin polymerization comprising A) at least one cyclopentadienyl complex of group 6 according to the invention, B) optionally an organic or inorganic support, C) optionally one or more activating compounds, D) optionally one or more catalysts suitable for olefin polymerization and E) optionally one or more metal compounds containing a metal of group 1, 2 or 13 of the Periodic Table.

Thus, more than one of the novel cyclopentadienyl complexes of group 6 can simultaneously be brought into contact with the olefin or olefins to be polymerized. This has the advantage that a wide range of polymers can be produced in this way. For example, bimodal products can be prepared in this way.

For the novel cyclopentadienyl complexes of group 6 to be able to be used in polymerization processes in the gas phase or in suspension, it is often advantageous for them to be used in the form of a solid, i.e. for them to be applied to a solid support B). Furthermore, the supported cyclopentadienyl complexes of group 6 have a high productivity. Consequently, the novel cyclopentadienyl complexes of group 6 can optionally be immobilized on an organic or inorganic support B) and used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polymers bearing polar functional groups, for example copolymers of ethene and acrylic esters, acrolein or vinyl acetate.

Particular preference is given to a catalyst system comprising a cyclopentadienyl complex of group 6 according to the invention and at least one activating compound C) together with a support component B).

To obtain such a supported catalyst system, the unsupported catalyst system can be reacted with a support component B). The order in which support component B), novel cyclopentadienyl complexes of group 6 A) and the activating compound C) are combined is in principle immaterial. The novel cyclopentadienyl complex of group 6 A) and the activating compound C) can be immobilized independently of one another or simultaneously. After the individual process steps, the solid can be washed with suitable inert solvents, e.g. aliphatic or aromatic hydrocarbons.

In a preferred method of preparing the supported catalyst system, at least one of the novel cyclopentadienyl complexes of group 6 is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported catalyst system comprising the cyclopentadienyl complex of group 6 is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277. In a further preferred embodiment, the activating compound C) is applied to the support component B) first and this supported compound is subsequently brought into contact with the novel cyclopentadienyl complex of group 6 A).

As support component B), preference is given to using finely divided supports which can be any organic or inorganic solid. In particular, the support component B) can be a porous support such as talc, a sheet silicate such as montmorillonite, mica, an inorganic oxide or a finely divided polymer powder (e.g. polyolefin or polymer bearing polar functional groups).

The support materials used preferably have a specific surface area in the range from 10 to 1000 m²/g, a pore volume in the range from 0.1 to 5 ml/g and a mean particle size of from 1 to 500 μm. Preference is given to supports having a specific surface area in the range from 50 to 700 m²/g, a pore volume in the range from 0.4 to 3.5 ml/g and a mean particle size in the range from 5 to 350 μm. Particular preference is given to supports having a specific surface area in the range from 200 to 550 m²/g, a pore volume in the range from 0.5 to 3.0 ml/g and a mean particle size of from 10 to 150 μm.

The inorganic support can be subjected to a thermal treatment, e.g. to remove adsorbed water. Such a drying treatment is generally carried out at from 80 to 800° C., preferably from 100 to 300° C., with drying at from 100 to 200° C. preferably being carried out under reduced pressure and/or under a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or SiCl₄, or else methylaluminoxane. Appropriate treatment methods are described, for example, in WO 00/31090.

The inorganic support material can also be chemically modified. For example, treatment of silica gel with NH₄SiF₆ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, AlPO₄, ZrO₂, TiO₂, B₂O₃ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. The silica gels can be dried and/or calcined before use.

Further preferred supports B) are hydrotalcites and calcined hydrotalcites. In mineralogy, hydrotalcite is a natural mineral having the ideal formula $$Mg_6Al_2(OH)_{16}CO_3 \cdot 4H_2O$$

whose structure is derived from that of brucite Mg(OH)₂. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the general formula $$M(II)_{2x}^{2+}M(III)_2^{3+}(OH)_{4x+4} \cdot A_{2/n}^{n-} \cdot zH_2O$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or B(OH)₄⁻ or polyoxo metal anions such as Mo₇O₂₄⁶⁻ or V₁₀O₂₈⁶⁻. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which, inter alia, the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1000° C., in particular from 400° C. to 700° C. It is possible for air or inert gas to be passed over the solid during calcination or for a vacuum to be applied.

On heating, the natural or synthetic hyrotalcites firstly give off water, i.e. drying occurs. On further heating, viz. the actual calcination, the metal hydroxides are converted into the metal oxides by elimination of hydroxyl groups and interstitial anions; OH groups or interstitial anions such as carbonate can also be present in the calcined hydrotalcites. A measure of this is the loss on ignition. This is the weight loss experienced by a sample which is heated in two steps, firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter D50 of from 5 to 200 μm, preferably from 10 to 150 μm, particularly preferably from 15 to 100 μm and in particular from 20 to 70 μm, and usually have pore volumes of from 0.1 to 10 cm$^3$/g, preferably from 0.2 to 5 cm$^3$/g, and specific surface areas of from 30 to 1000 m$^2$/g, preferably form 50 to 800 m$^2$/g and in particular from 100 to 600 m$^2$/g. The novel cyclopentadienyl complexes of group 6 are preferably applied in such an amount that the concentration of the transition metal complex in the finished catalyst system is from 5 to 200 μmol, preferably from 20 to 100 μmol and particularly preferably from 25 to 70 μmol, per g of support B).

Some of the novel monocyclopentadienyl complexes of group 6 have little polymerization activity on their own and are then brought into contact with an activator, viz. the component C), in order to able to display good polymerization activity. For this reason, the catalyst system optionally further comprises, as component C), one or more activating compounds, preferably at least one cation-forming compound C).

Suitable compounds C) which are able to react with the cyclopentadienyl complexes of group 6 A) to convert them into catalytically active, or more active, compounds are, for example, compounds such as an aluminoxane, a strong uncharged Lewis acid, an ionic compound having a Lewis acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the general formulae (X) or (XI)

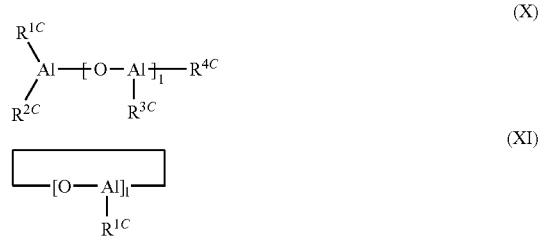

where R$^{1C}$-R$^{4C}$ are each, independently of one another, a C$_1$-C$_6$-alkyl group, preferably a methyl, ethyl, butyl or isobutyl group, and l is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that l is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the general formula (X) or (XI).

It has been found to be advantageous to use the cyclopentadienyl complexes of group 6 A) and the aluminoxane compounds in such amounts that the atomic ratio of aluminum from the aluminoxane compounds including any aluminum alkyl still present to the transition metal from the cyclopentadienyl complex of group 6 A) is in the range from 1:1 to 1000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the cyclopentadienyl complex of group 6 A) is usually in the range from 1:1 to 100:1, preferably from 10:1 to 50:1 and in particular in the range from 20:1 to 40:1. Preference is in this case given to using a cyclopentadienyl metal dialkyl compound A).

As strong, uncharged Lewis acids, preference is given to compounds of the general formula (XII)

where

M$^{1C}$ is an element of group 13 of the Periodic Table of the Elements, in particular B, Al or Ga, preferably B, X$^{1C}$, X$^{2C}$ and X$^{3C}$ are each hydrogen, C$_1$-C$_{10}$-alkyl, C$_6$-C$_{15}$-aryl, alkylaryl, arylalkyl, haloalkyl or haloaryl each having from 1 to 10 carbon atoms in the alkyl part and from 6 to 20 carbon atoms in the aryl part or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins, e.g. trialkylborane, triarylborane or trimethylboroxin. Particular preference is given to using boranes which bear at least two perfluorinated aryl radicals. Particular preference is given to compounds of the general formula (XII) in which X$^{1C}$, X$^{2C}$ and X$^{3C}$ are identical, preferably tris(pentafluorphenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2,2',3,3',4',5,5',6,6'-nonafluorobiphenyl, triethylaluminum/pentafluorophenol and triisobutylaluminum/pentafluorophenol and triethylaluminium/4,4'-dihydroxy-2,2',3,3',5,5',6,6'-octafluorobiphenyl hydrate.

In further suitable aluminum and boron compounds of the formula (XII), $X^{1C}$ is an OH group, as in, for example, boronic acids and borinic acids, in particular borinic acids having perfluorinated aryl radicals, for example $(C_6F_5)_2$BOH.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the general formula (XIII)

where
$M^{2C}$ is an element of groups 1 to 16 of the Periodic Table of the Elements,
$Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl part and from 1 to 28 carbon atoms in the alkyl part, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is an integer from 0 to 5,
d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcylohexylammonium and N,N-dimethylbenzylammonium and also derivatives of the latter two.

Compounds containing anionic boron heterocycles as described in WO 9736937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or for a borate anion to be joined to a borane, as in the dianion $[(C_6F_5)_3B-C_6F_4-B(C_6F_5)_3]^{2-}$ or the anion $[(C_6F_5)_3B-CN-B(C_6F_5)_3]^-$, or the borate anion can be bound via a bridge bearing a suitable functional group to the support surface.

Further suitable activating compounds C) are listed in WO 00/31090.

The amount of strong, uncharged Lewis acids, ionic compounds having Lewis acid cations or ionic compounds containing Brönsted acids as cations is preferably from 0.1 to 20 equivalents, more preferably from 1 to 10 equivalents, based on the monocyclopentadienyl complex A).

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the cyclopentadienyl complexes of group 6 A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, e.g. by means of carbon tetrachloride. The preparation of such systems is described, for example, in WO 01/41920.

A likewise broad product spectrum can be achieved by use of the novel cyclopentadienyl complexes of group 6 A) in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups 3 to 12 of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl radicals and ligands which are free of cyclopentadienyl radicals. A large number of such compounds B) suitable for olefin polymerization are described in Chem. Rev. 2000, Vol. 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene complexes. Particularly useful metallocene complexes are those of the general formula (XIV)

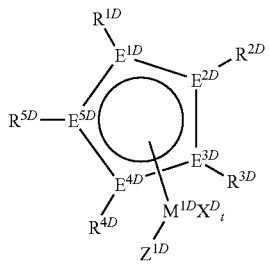

(XIV)

where the substituents and indices have the following meanings:

$M^{1D}$ is titanium, zirconium, hafnium, vanadium, niobium, tantalum, chromium, molybdenum or tungsten, or an element of group 3 of the Periodic Table and the lanthanides, $X^D$ is fluorine, chlorine, bromine, iodine, hydrogen, $C_1$-$C_{10}$-alkyl, $C_2$-$C_{10}$-alkenyl, $C_6$-$C_{15}$-aryl, arylalkyl having from 1 to 10 carbon atoms in the alkyl part and 6-20 carbon atoms in the aryl part, —$OR^{6D}$ or —$NR^{6D}R^{7D}$, or two radicals $X^D$ for a substituted or unsubstituted diene ligand, in particular a 1,3-diene ligand, and the radicals $X^D$ are identical or different and may be joined to one another, $E^{1D}$-$E^{5D}$ are each carbon or not more than $E^{10}$ to $E^{50}$ is phosphorus or nitrogen, preferably carbon, t is 1, 2 or 3 and is such that, depending on the valence of $M^{1D}$, the metallocene complex of the general formula (XIV) is uncharged, where $R^{6D}$ and $R^{7D}$ are each $C_1$-$C_{10}$-alkyl, $C_6$-$C_{15}$-aryl, alkylaryl, arylalkyl, fluoroalkyl or fluoroaryl each having from 1 to 10 carbon atoms in the alkyl part and from 6 to 20 carbon atoms in the aryl part and $R^{1D}$ to $R^{5D}$ are each, independently of one another, hydrogen, $C_1$-$C_{22}$-alkyl, 5 to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^{8D}{}_2$, $N(SiR^{8D}{}_3)_2$, $OR^{8D}$, $OSiR^{8D}{}_3$, $SiR^{8D}{}_3$, where the organic radicals $R^{1D}$-$R^{5D}$ may also be substituted by halogen and/or two radicals $R^{1D}$-$R^{5D}$, in particular vicinal radicals, may also be joined to form a five-, six- or seven-membered ring and/or two vicinal radicals $R^{1D}$-$R^{5D}$ may be joined to form a five-, six- or seven-membered heterocycle which contains at least one atom from the group consisting of N, P, O and S, where the radicals $R^{8D}$ can be identical or different and are each $C_1$-$C_{10}$-alkyl, $C_3$-$C_{10}$-cycloalkyl, $C_6$-$C_{15}$-aryl, $C_1$-$C_4$-alkoxy or $C_1$-$C_{10}$-aryloxy and $Z^{1D}$ is $X^D$ or

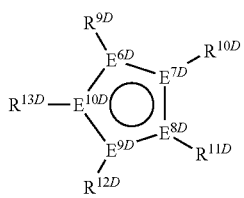

where the radicals $R^{9D}$ to $R^{13D}$ are each, independently of one another, hydrogen, $C_1$-$C_{22}$-alkyl, 5- to 7-membered cycloalkyl or cycloalkenyl which may in turn bear $C_1$-$C_{10}$-alkyl as substituents, $C_2$-$C_{22}$-alkenyl, $C_2$-$C_{22}$-aryl, arylalkyl having from 1 to 16 carbon atoms in the alkyl part and 6-21 carbon atoms in the aryl part, $NR^{14D}{}_2$, $N(SiR^{14D}{}_3)_2$, $OR^{14D}$, $OSiR^{14D}{}_3$, $SiR^{14D}{}_3$, where the organic radicals $R^{9D}$-$R^{13D}$ may also be substituted by halogens and/or two radicals $R^{9D}$-$R^{13D}$, in particular vicinal radicals, may also be joined to form a five-, six- or seven-membered ring and/or two vicinal radicals $R^{9D}$-$R^{13D}$ may be joined to form a five-, six- or seven-membered heterocycle which contains at least one atom from the group consisting of N, P, O and S, where the radicals $R^{14D}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6D}$-$E^{10D}$ are each carbon or not more than one $E^{8D}$ to $E^{10D}$ is phosphorus or nitrogen, preferably carbon, or the radicals $R^{4D}$ and $Z^{1D}$ together form an —$R^{15D}{}_v$-$A^{1D}$- group in which $R^{15D}$ is

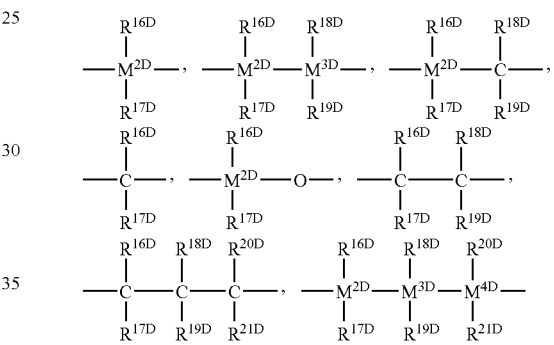

=$BR^{16D}$, =$BNR^{16D}R^{17D}$, $AlR^{16D}$, —Ge—, —Sn—, —O—, —S—, =SO, =$SO_2$, =$NR^{16D}$, =CO, $PR^{16D}$ or =$P(O)R^{16D}$, where $R^{18D}$-$R^{21D}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them forming a saturated or unsaturated ring having from 4 to 15 carbon atoms, and $M^{2D}$-$M^{4D}$ are each silicon, germanium or tin, preferably silicon, $A^{1D}$ is

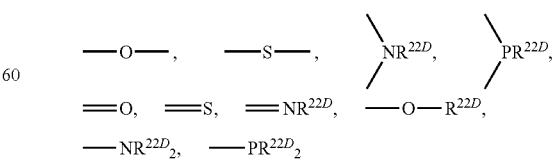

or an unsubstituted, substituted or fused, heterocyclic ring system, where the radicals $R^{22D}$ are each, independently of one another, $C_1$-$C_{10}$-alkyl, $C_6$-$C_{15}$-aryl, $C_3$-$C_{10}$-cycloalkyl, $C_7$-$C_{18}$-arylalkyl or $Si(R^{23D})_3$, $R^{23D}$ is hydrogen, $C_1$-$C_{10}$-alkyl, $C_6$-$C_{15}$-aryl, which may in turn bear $C_1$-$C_4$-alkyl groups as substituents or $C$—, $C_{1-10}$-cycloalkyl, v is 1 or when $A^{1D}$ is an unsubstituted, substituted or fused heterocyclic ring system may also be 0, or the radicals $R^{4D}$ and $R^{12D}$ together form a —$R^{15D}$— group.

$A^{1D}$ together with the bridge $R^{15D}$ can, for example, form an amine, ether, thioether or phosphine, However, $A^{1D}$ may also be an unsubstituted, substituted or fused, heterocyclic aromatic ring system which in addition to carbon ring atoms can contain heteroatoms from the group consisting of oxygen, sulfur, nitrogen and phosphorus. Examples of 5-membered heteroaryl groups which contain from 1 to 4 nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which can contain from one to four nitrogen atoms and/or a phosphorus atom are 2-pyridinyl, 2-phosphaphenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

It is preferred that the radicals $X^D$ in the general formula (XIV) are identical, preferably fluorine, chlorine, bromine, $C_1$-$C_7$-alkyl or aralkyl, in particular chlorine, methyl or benzyl.

The synthesis of such complexes can be carried out by methods known per se, preferably by reaction of the appropriately substituted, cyclic hydrocarbon anions with halides of titanium, zirconium, hafnium or chromium.

Among the metallocene complexes of the general formula (XIV) preference is given to

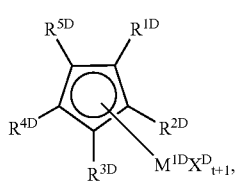

(XIVa)

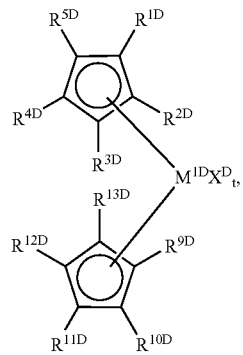

(XIVb)

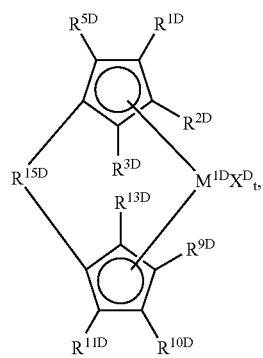

(XIVc)

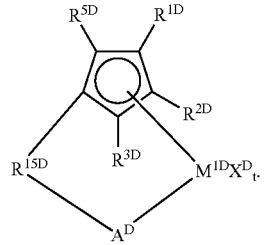

(XIVd)

Among the compounds of the formula (XIVa), particular preference is given to those in which $M^{1D}$ is titanium, vanadium or chromium, $X^D$ is chlorine, $C_1$-$C_4$-alkyl, phenyl, alkoxy or aryloxy, t is 1 or 2 and $R^{1D}$ to $R^{5D}$ are each hydrogen, $C_1$-$C_6$-alkyl or two adjacent radicals $R^{1D}$ to $R^{5D}$ form a substituted or unsubstituted benzo group.

Among the compounds of the formula (XIVb), preference is given to those in which $M^{1D}$ is titanium, zirconium, vanadium, hafnium or chromium, $X^D$ is fluorine, chlorine, $C_1$-$C_4$-alkyl or benzyl, or two radicals $X^D$ form a substituted or unsubstituted butadiene ligand, t is 0 in the case of chromium, otherwise 1 or 2, preferably 2, $R^{1D}$ to $R^{5D}$ are each hydrogen, $C_1$-$C_8$-alkyl, $C_6$-$C_8$-aryl, $NR^{8D}_2$, $OSiR^{8D}_3$ or $Si(R^{8D})_3$ and $R^{9D}$ to $R^{13D}$ are each hydrogen, $C_1$-$C_8$-alkyl or $C_1$-$C_8$-aryl, $NR^{14D}_2$, $OSiR^{14D}_3$ or $Si(R^{14D})_3$ or two radicals $R^{1D}$ to $R^{5D}$ and/or $R^{9D}$ to $R^{13D}$ together with the $C_5$ ring form an indenyl, fluorenyl or substituted indenyl or fluorenyl system.

The compounds of the formula (XIVb) in which the cyclopentadienyl radicals are identical are particularly useful.

Examples of particularly useful compounds D) of the formula (XIVb) include: bis(cyclopentadienyl)chromium, bis(indenyl)titanium dichloride, bis(fluorenyl)titanium dichloride, bis(tetrahydroindenyl)titanium dichloride, bis(pentamethylcyclopentadienyl)titanium dichloride, bis(trimethylsilylcyclopentadienyl)titanium dichloride, bis(trimethoxysilylcyclopentadienyl)titanium dichloride, bis(isobutylcyclopentadienyl)titanium dichloride, bis(3-butenycyclopentadienyl)titanium dichloride, bis(methylcyclopentadienyl)titanium dichloride, bis(1-,3-di-tert-butylocyclopentadienyl)-titanium dichloride, bis(trifluoromethylcyclopentadienyl)titanium dichloride, bis(tert-butylcyclopentadienyl)titanium dichloride, bis(n-butylcyclopentadienyl)titanium dichloride, bis(phenylcyclopentadienyl)titanium dichloride, bis(N,N-dimethylaminomethylcyclopentadienyl)titanium dichloride, bis(1,3-dimethylcyclopentadienyl)titanium dichloride, bis(1-methyl-3-n-butylcyclopentadienyl)titanium dichloride, (cyclopentadienyl)(methylcyclopentadienyl)titanium dichloride, (cyclopentadienyl)(n-butylcyclopentadienyl)titanium dichloride, (methylcyclopentadienyl)(n-butylcyclopentadienyl)titanium dichloride, (cyclopentadienyl)(1-methyl-3-n-butylcyclopentadienyl)titanium dichloride, bis(cyclopentadienyl)zirconium dichloride, bis(pentamethylcyclopentadienyl)zirconium dichloride, bis(methylcyclopentadienyl)zirconium dichloride, bis(ethylcyclopentadienyl)zirconium dichloride, bis(n-butylcyclopentadienyl)zirconium dichloride, bis(tert-butylcyclopentadienyl)zirconium dichloride, bis(isobutylcyclopentadienyl)zirconium dichloride, bis(3-butenylcyclopentadienyl)-zirconium dichloride, bis(trifluoromethylcyclopentadienyl)zirconium dichloride, bis(phenylcyclopentadienyl)zirconium dichloride, bis(1,3-dimethylcyclopentadienyl)zirconium dichloride, bis(1-n-butyl-3-methylcyclopentadienyl)zirconium dichloride, bis(1,3-di-tert-butylcyclopentadienyl)zirconium dichloride, bis(tetramethylcyclopentadienyl)zirconium dichloride, bis(indenyl)zirconium dichloride, bis(tetrahydroindenyl)zirconium dichloride, bis(fluorenyl)zirconium dichloride, (cyclopentadienyl)(methylcyclopentadienyl)zirconium dichloride, (cyclopentadienyl)(n-butylcyclopentadienyl)zirconium dichloride, (methylcyclopentadienyl)(n-butylcyclopentadienyl)zirconium dichloride, (cyclopentadienyl)(1-methyl-3-n-butylcyclopentadienyl)zirconium dichloride, bis(trimethoxysilylcyclopentadienyl)zirconium dichloride and bis(trimethylsilylcyclopentadienyl)zirconium dichloride, and also the corresponding dimethylzirconium compounds.

Particularly useful compounds of the formula (XIVc) are those in which
$R^{15D}$ is

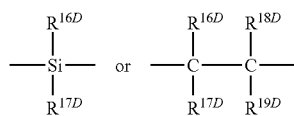

or $=BR^{16D}$ or $=BNR^{16D}R^{17D}$, $M^{1D}$ is titanium, zirconium or hafnium, in particular zirconium, and the radicals $X^D$ are identical or different and are each chlorine, $C_1$-$C_4$-alkyl, benzyl, phenyl or $C_7$-$C_{15}$-alkylaryloxy.

Particularly useful compounds of the formula (XIVc) are those of the formula (XIVc')

where

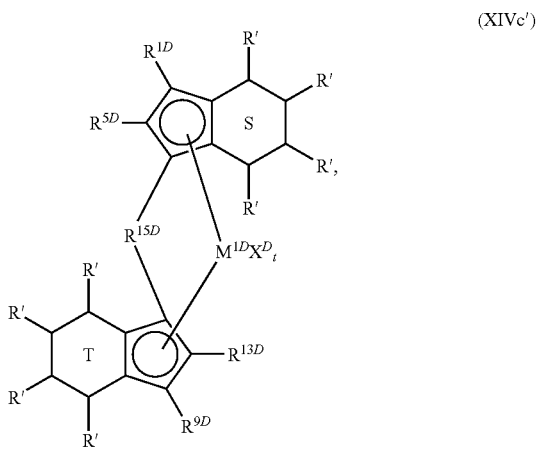

the radicals R' are identical or different and are each hydrogen, $C_1$-$C_{10}$-alkyl or $C_3$-$C_{10}$-cycloalkyl, preferably methyl, ethyl, isopropyl or cyclohexyl, $C_6$-$C_{20}$-aryl, preferably phenyl, naphthyl or mesityl, $C_7$-$C_{40}$-arylalkyl, $C_7$-$C_{40}$-alkylaryl, preferably 4-tert-butylphenyl or 3,5-di-tert-butylphenyl, or $C_8$-$C_{40}$-arylalkenyl, $R^{5D}$ and $R^{13D}$ are identical or different and are each hydrogen, $C_1$-$C_6$-alkyl, preferably methyl, ethyl, isopropyl, n-propyl, n-butyl, n-hexyl or tert-butyl, and the rings S and T are identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6 positions, the 2,4,6 positions, the 2,5,6 positions, the 2,4,5,6 positions or the 2,4,5,6,7 positions, in particular in the 2,4 positions, with the following numbering applying to the site of substitution:

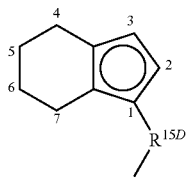

Furthermore, preference is given to using bridged bisindenyl complexes in the rac or pseudo-rac form as component D). The term "pseudo-rac form" refers to complexes in which the two indenyl ligands are in the rac arrangement relative to one another when all other substituents of the complex are disregarded.

Further examples of particularly-useful catalysts D) (XIVc) and (XIVc') include: methylenebis(cyclopentadienyl)zirconium dichloride, methylenebis(3-methylcyclopentadienyl)-zirconium dichloride, methylenebis(3-n-butylcyclopentadienyl)zirconium dichloride, methylenebis(indenyl)zirconium dichloride, methylenebis(tetrahydroindenyl)zirconium dichloride, isopropylidenebis(cyclopentadienyl)zirconium dichloride, isopropylidenebis(3-trimethylsilylcyclopentadienyl)zirconium dichloride, isopropylidenebis(3-methylcyclopentadienyl)zirconium dichloride, isopropylidenebis(3-n-butylcyclopentadienyl)

zirconium dichloride, isopropylidenebis(3-phenylcyclopentadienyl)zirconium dichloride, isopropylidenebis(indenyl)zirconium dichloride, isopropylidenebis(tetrahydroindenyl)zirconium dichloride, dimethylsilanediylbis(cyclopentadienyl)-zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluorenylcyclopentadienylzirconium dichloride, dimethylsilanediylbis-(tetramethylcyclopentadienyl)zirconium dichloride, dimethylsilanediylbis(3-trimethylsilylcyclopentadienyl)zirconium dichloride, dimethylsilanediylbis(3-methylcyclopentadienyl)zirconium dichloride, dimethylsilanediylbis(3-n-butylcyclopentadienyl)zirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(2-methylindenyl)-zirconium dichloride, dimethylsilanediylbis(2-isopropylindenyl)zirconium dichloride, dimethylsilanediylbis(2-tert-butylindenyl)zirconium dichloride, diethylsilanediylbis(2-methylindenyl)zirconium dibromide, dimethylsilanediylbis(3-methyl-5-methylcyclopentadienyl)zirconium dichloride, dimethylsilenediylbis(3-ethyl-5-isopropylcyclopentadienyl)zirconium dichloride, dimethylsilanediylbis(2-ethylindenyl)zirconium dichloride, dimethylsilanediylbis(2-methyl-4,5-benzindenyl)-zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis(2-methyl-4-(1-naphthyl)-indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride, dimethylsilanediylbis(2-i-butyl-4-(1-naphthyl)-indenyl)zirconium dichloride, dimethylsilanediylbis(2-propyl-4-(9-phenanthryl)indenyl)zirconium dichloride, dimethylsilanediylbis(2-methyl-4-isopropylindenyl)zirconium dichloride, dimethylsilanediylbis(2,7-dimethyl-4-isopropylindenyl)zirconium dichloride, dimethylsilanediylbis(2-methyl-4,6-diisopropylindenyl)zirconium dichloride, dimethylsilanediylbis(2-methyl-4-[p-trifluoromethylphenyl]indenyl)zirconium dichloride, dimethylsilanediylbis(2-methyl-4-[3',5'-dimethylphenyl]-indenyl)zirconium dichloride, dimethylsilanediylbis(2-methyl-4-[4'-tert-butylphenyl]indenyl)zirconium dichloride, diethylsilanediylbis(2-methyl-4-[4'-tert-butylphenyl]indenyl)zirconium dichloride, dimethylsilanediylbis(2-ethyl-4-[4'-tert-butylphenyl]indenyl)zirconium dichloride, dimethylsilanediylbis(2-propyl-4-[4'-tert-butylphenyl]indenyl) zirconium dichloride, dimethylsilanediylbis(2-isopropyl-4-[4'-tert-butylphenyl]indenyl)zirconium dichloride, dimethylsilanediylbis(2-n-butyl[4'-tert-butylphenyl]indenyl)zirconium dichloride, dimethylsilanediylbis(2-hexyl-4-[4'-tert-butylphenyl]indenyl)zirconium dichloride, dimethylsilanediyl(2-isopropyl-2-methyl-4-phenylindenyl)zirconium dichloride, dimethylsilanediyl(2-isopropyl-4-(1-naphthyl)indenyl)(2-methyl-4-(1-naphthyl)indenyl)zirconium dichloride, dimethylsilanediyl(2-isopropyl-4-[4'-tert-butylphenyl]indenyl)(2-methyl-4-[4'-tert-butylphenyl]indenyl)zirconium dichloride, dimethylsilanediyl-(2-isopropyl-4-[4'-tert-butylphenyl]indenyl)(2-ethyl-4-[4'-tert-butylphenyl]indenyl)zirconium dichloride, dimethylsilanediyl(2-isopropyl-4-[4'-tert-butylphenyl]indenyl)(2-methyl-4-[3',5-bis-tert-butylphenyl]indenyl)zirconium dichloride, dimethylsilanediyl(2-isopropyl-4-[4'-tert-butylphenyl]indenyl)(2-methyl-4-[1'-naphthyl]indenyl)zirconium dichloride and ethylene(2-isopropyl-4'-tert-butylphenylindenyl)(2-methyl-4-[4'-tert-butylphenyl]indenyl)zirconium dichloride, and also the corresponding dimethylzirconium, monochloromono(alkylaryloxy)zirconium and di(alkylaryloxy)zirconium compounds. The complexes are preferably used in the rac form.

Such complexes can be synthesized by methods known per se, preferably by reacting the appropriately substituted, cyclic hydrocarbon anions with halides of titanium, zirconium, hafnium, vanadium, niobium, tantalum or chromium. Examples of appropriate preparative methods are described, inter alia, in Journal of Organometallic Chemistry, 369 (1989), 359-370.

Particularly useful compounds of the general formula (XIVd) are those in which $M^{1D}$ is titanium or zirconium, in particular titanium, and $X^D$ is chlorine, $C_1$-$C_4$-alkyl or phenyl or two radicals $X^D$ form a substituted or unsubstituted butadiene ligand, $R^{15D}$ is

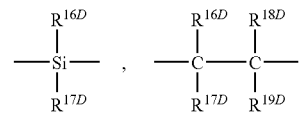

or $=BR^{16D}$ or $=BNR^{16D}R^{17D}$, $A^{1D}$ is

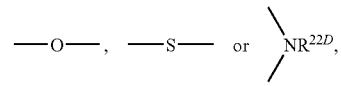

t is 1 or 2, preferably 2, $R^{1D}$ to $R^{3D}$ and $R^{5D}$ are each hydrogen, $C_1$-$C_{10}$-alkyl, preferably methyl, $C_3$-$C_{10}$-cycloalkyl, $C_6$-$C_{15}$-aryl, $NR^{8D}{}_2$ or $Si(R^{8D})_3$, or two adjacent radicals form a cyclic group having from 4 to 12 carbon atoms, with particular preference being given to all $R^{1D}$ to $R^{3D}$ and $R^{5D}$ being methyl.

Particularly useful complexes D) of the formula (XIVd) are dimethylsilanediyl(tetramethylcyclopentadienyl)(phenylamino)titanium dichloride, dimethylsilanediyl(tetramethylcyclopentadienyl)(benzylamino)titanium dichloride, dimethylsilanediyl(tetramethylcyclopentadienyl)(tert-butylamino)titanium dichloride, dimethylsilanediyl (tetramethylcyclopentadienyl)(adamantyl)titanium dichloride and dimethylsilanediyl(indenyl)(tert-butylamino) titanium dichloride.

Another group of compounds of the formula (XIVd) which are particularly useful are those in which $M^{1D}$ is titanium, vanadium or chromium, preferably in the oxidation state III and $X^D$ is chlorine, $C_1$-$C_4$-alkyl or phenyl or two radicals $X^D$ form a substituted or unsubstituted butadiene ligand, $R^{15D}$ is

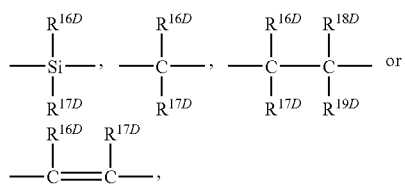

$A^{1D}$ is $O-R^{22D}$, $-NR^{22D}{}_2$, $-PR^{22D}{}_2$ or an unsubstituted, substituted or fused, heterocyclic, in particular heteroaromatic, ring system, v is 1 or when $A^{1D}$ is an unsubstituted, substituted or fused, heterocyclic ring system may be 0 or 1 and $R^{1D}$ to $R^{3D}$ and $R^{5D}$ are each hydrogen, $C_1$-$C_{10}$-alkyl, $C_3$-$C_{10}$-cycloalkyl, $C_9$-$C_{15}$-aryl or $Si(R^{8D})_3$, or two adjacent radicals form a cyclic group having from 4 to 12 carbon atoms.

In a preferred embodiment, $A^{1D}$ is an unsubstituted, substituted or fused, heteroaromatic ring system and $M^{1D}$ is chromium. Very particular preference is given to $A^{1D}$ being an unsubstituted or substituted, e.g. alkyl-substituted, in particular substituted or unsubstituted quinolyl or pyridyl bound in position 8 or 2, e.g. 8-quinolyl, 8-(2-methylquinolyl), 8-(2,3,4-trimethylquinolyl), 8-(2,3,4,5,6,7-hexamethylquinolyl), v being 0 and MID being chromium. Preferred catalysts D) of this type are 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methylcyclopentadienylchromium (III) dichloride, 1-(8-quinolyl)-2,3,4,5-tetramethylcyclopentadienylchromium(III) dichloride, 1-(8-quinolyl)tetrahydroindenylchromium(III) dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl) benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl))-2,3,4,5-tetramethylcyclopentadienylchromium(III) dichloride, 1-(8-(2-methylquinolyl))tetrahydroindenylchromium(III) dichloride, 1-(8-(2-methylquinolyl))indenylchromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) dichloride, 1-(8-(2-methylquinolyl))benzindenylchromium (III) dichloride, 1-(2-pyridylmethyl)indenylchromium(III) dichloride or 1-(8-(2-methylquinolyl))-2-methylbenzindenylchromium(III) dichloride.

Furthermore, owing to the ease of preparation, preference is given to compounds in which $R^{15D}$ is CH=CH or 1,2-phenylene and $A^{1D}$ is $NR^{22D}{}_2$, and compounds in which $R^{15D}$ is $CH_2$, $C(CH_3)_2$ or $Si(CH_3)_2$ and $A^{1D}$ is unsubstituted or substituted 2- or 8-quinolyl or unsubstituted or substituted 2-pyridyl.

The preparation of such functional cyclopentadienyl ligands has been known for a long time. Various synthetic routes to these complexing ligands are described, for example, by M. Enders et. al. in Chem. Ber. (1996), 129, 459-463, or P. Jutzi and U. Siemeling in J. Orgmet. Chem. (1995), 500, 175-185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed by a cyclopentadienyl or heterocyclopentadienyl and a fused on heterocycle, with the heterocycles preferably being aromatic and containing nitrogen and/or sulfur. Such compounds are described, for example, in WO 98/22486. These are, in particular, dimethylsilanediyl(2-methylphenylindenyl)(2,5-dimethyl-N-phenyl-4-azapentalene)zirconium dichloride, dimethylsilanediylbis(2-methyl-4-phenyl-4-hydroazulenyl)zirconium dichloride, dimethylsilanediylbis(2-ethyl-4-phenyl-4-hydroazulenyl)zirconium dichloride, bis(2,5-dimethyl-N-phenyl-4-azapentalene)zirconium dichloride or (indenyl)(2,5-dimethyl-N-phenyl-4-azapentalene)zirconium dichloride.

Further suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5-tri(methyl)-1,3,5-triazacyclohexane]chromium trichloride, [1,3,5-tri(ethyl)-1,3,5-triazacyclohexane]chromium trichloride, [1,3,5-tri(octyl)-1,3,5-triazacyclohexane]chromium trichloride, [1,3,5-tri(dodecyl)-1,3,5-triazacyclohexane]chromium trichloride and [1,3,5-tri(benzyl)-1,3,5-triazacyclohexane]chromium trichloride.

Further suitable catalysts D) are, for example, transition metal complexes with at least one ligand of the general formulae XV to XIX,

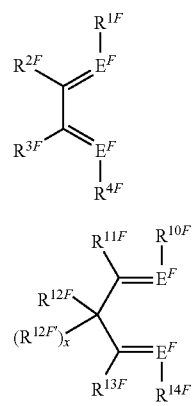

-continued

XVII $$\begin{array}{c} R^{8F} \\ R^{9F} \\ \parallel \\ E^F \\ | \\ (CR_2{}^{7F})_y \\ | \\ E^F \\ \parallel \\ R^{5F} \\ R^{6F} \end{array}$$

XVIII $$\begin{array}{c} R^{15F} \\ | \\ H \\ | \\ O \\ R^{16F} \\ R^{17F} \\ E^F \\ | \\ O \\ | \\ H \\ | \\ R^{18F} \end{array}$$

XIX $$\left[ \begin{array}{c} R^{22F} \\ R^{21F} \\ R^{20F} \\ E^F \\ R^{19F} \end{array} \right]$$

where the transition metal is selected from among the elements Ti, Zr, Hf, Sc, V, Nb, Ta, Cr, Mo, W, He, Co, Ni, Pd. Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three atoms $E^F$ in a molecule can be identical or different.

The radicals $R^{1F}$ to $R^{25F}$, which may be identical or different within a ligand system XV to XIX, are as follows:

$R^{1F}$ and $R^{4F}$ are each, independently of one another, a hydrocarbon radical or a substituted hydrocarbon radical, preferably a hydrocarbon radical in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{1F}$ may also form a ring system in which one or more heteroatoms may also be present, $R^{6F}$ and $R^{8F}$ are each, independently of one another, a hydrocarbon radical or a substituted hydrocarbon radical, $R^{5F}$ and $R^{9F}$ are each, independently of one another, hydrogen, a hydrocarbon radical or a substituted hydrocarbon radical, where $R^{6F}$ and $R^{5F}$ or $R^{8F}$ and $R^{9F}$ may together also form a ring system, the radicals $R^{7F}$ are each, independently of one another, hydrogen, a hydrocarbon radical or a substituted hydrocarbon radical, where two $R^{7F}$ may together also form a ring system, $R^{10F}$ and $R^{14F}$ are each, independently of one another, a hydrocarbon radical or a substituted hydrocarbon radical, $R^{11F}$, $R^{12F}$, $R^{12F'}$ and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may together also form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$-$C_{20}$-alkenyl, $C_6$-$C_{20}$-aryl, arylalkyl having from 1 to 10 carbon atoms in the alkyl part and 6-20 carbon atoms in the aryl part, where the organic radicals $R^{19F}$ and $R^{25F}$ may also substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{26F}{}_3$, where the organic radicals $R^{20F}$-$R^{24F}$ may also be substituted by halogens and two vicinal radicals $R^{20F}$-$R^{24F}$ may also be joined to form a five- or six-membered ring and the radicals $R^{26F}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{26F}$ may also be joined to form a five- or six-membered ring, x is 0 or 1, with the complex of the formula (XVI) being negatively charged when x is 0 and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.:

di(2,6-di-i-propylphenyl)-2,3-dimethyldiazabutadienepalladium dichloride, di(di-i-propylphenyl)-2,3-dimethyldiazabutadienenickel dichloride, di(2,6-di-i-propylphenyl)dimethyldiazabutadienedimethylpalladium, di(2,6-di-i-propylphenyl)-2,3-dimethyl-diazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadienedimethylpalladium, di(2,6-dimethylphenyl)-2,3-dimethyldiazabutadiendimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'- bipyridylpalladium dichloride, 1,1-bipyridylnickel dichloride, 1,1'-bipyridyl(dimethyl)palladium, 1,1'-bipyridyl (dimethyl)nickel.

Particularly useful compounds (XIX) also include those which are described in J. Am. Chem. Soc. 120, p. 4049 ff. (1998), J. Chem. Soc., Chem. Commun. 1998, 849, and WO 98/27124. $E^F$ is preferably nitrogen and $R^{19F}$ and $R^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl and 2,4,6-trimethylphenyl. At the same time, $R^{20F}$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands F—XIX with the transition metals Fe, Co or Ni, in particular Fe. Particular preference is given to 2,6-diacetylpyridinebis(2,4-dimethylphenylimine) iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis (2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenyl)cobalt dichloride, 2,6-diacetylpyridinbis(2,6-diisopropylphenylimine)cobalt dichloride, 2,6-diacetylpyridinebis(2,6-dichlorophenylimine)cobalt dichloride and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with Pi ligands having one or more heteroatoms in the Pi system, for example the boratabenzene ligand, the pyrrolyl anion or the phospholyl anion, can also be used as catalysts D).

Further complexes which are suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one cyclopentadienyl complex of group 6 A) in the presence of at least one further catalyst D) customary for the polymerization of olefins and, if desired, one or more activating compounds C). Here, depending on the catalyst combinations A) and D), one or more activating compounds C) may be advantageous. The polymerization catalysts D) can likewise be supported and can be used simultaneously or in any order with the complex A) of the invention. For example, the cyclopentadienyl complex of group 6 A) and the polymerization catalysts D) can be applied together to a support B) or to different supports B). It is also possible to use mixtures of various catalysts as component D). The molar ratio of transition metal complex A) to polymerization catalyst D) is usually in the range from 1:100 to 100:1, preferably from 1:10 to 20:1 and particularly preferably from 1:1 to 10:1.

The catalyst system may further comprise, as additional component E); a metal compound of the general formula (XX),

$$M^G(R^{1G})_{r^G}(R^{2G})_{s^G}(R^{3G})_{t^G} \qquad (XX)$$

where
$M^G$ is Li, Na, K, Be, Mg, Ca, Sr, Ba, boron, aluminum, gallium, indium, thallium, zinc in particular Li, Na, K, Mg, boron, aluminum or Zn,
$R^{1G}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part,
$R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl part and from 6 to 20 carbon atoms in the aryl part, or alkoxy with $C_1$-$C_{10}$-alkyl or $C_6$-$C_{15}$-aryl,
$r^G$ is an integer from 1 to 3
and
$s^G$ and $t^G$ are integers from 0 to 2, with the sum $r^G+s^G+t^G$ corresponding to the valence of $M^G$, where the component E) is not identical to the component C). It is also possible to use mixtures of various metal compounds of the formula (XX).

Among the metal compounds of the general formula (XX), preference is given to those in which
$M^G$ is lithium, magnesium, boron or aluminum and
$R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from cyclopentadienyl complex of group 6 A) is from 2000:1 to 0.1:1, preferably from 800:1 to 0.2:1 and particularly preferably from 100:1 to 1:1.

In general, the catalyst solid together with the further metal compound E) of the general formula (XX), which may be different from the metal compounds E) used in the preparation of the catalyst solid, is used as constituent of a catalyst system for the polymerization or copolymerization of olefins. It is also possible, particularly when the catalyst solid does not contain an activating component C) for the catalyst system to further comprise, in addition to the catalyst solid, one or more activating compounds C) which are identical to or different from any activating compounds C) present in the catalyst solid.

To prepare the catalyst systems of the invention, preference is given to immobilizing at least one of the components A) and/or C) on the support B) by physisorption or by means of a chemical reaction, i.e. covalent binding of the components, with reactive groups on the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment, the cyclopentadienyl complex of group 6 A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of industrial implementation of the above process are described in WO 96/00243, WO 98/40419 or WO 00/05277. A further preferred embodiment comprises firstly applying the activating compound C) to the support B) and subsequently bringing this supported activating compound into contact with the cyclopentadienyl complex of group 6 A).

The component D) can likewise be reacted in any order with the components A) and optionally B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the α-olefin to be polymerized and the catalyst solid comprising the components A), B) and C) as described above subsequently being added. The cyclopentadienyl complex of group 6 A) can be brought into contact with the component(s) C) and/or D) either before or after being brought into contact with the olefins to be polymerized. Preactivation using one or more components C) prior to mixing with the olefin and further addition of the same or different components C) and/or D) after the mixture has been brought into contact with the olefin is also possible. Preactivation is generally carried out at temperatures of 10-100° C., preferably 20-80° C.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer to be polymerized onto it is usually in the range from 1:0.1 to 1:1000, preferably from 1:1 to 1:200.

Furthermore, a small amount of an olefin, preferably a α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1000 to 1000:1, preferably from 1:5 to 20:1.

The catalyst systems of the invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic acid or methacrylic acid, for example acrylates, methacrylates or acrynitrile, or vinyl esters, for example vinyl acetate. Preference is given to nonpolar olefinic compounds, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene or methylnorbornene or dienes such as 5-ethylidene-2-norbornene, norbornadiene and ethylnorbornadiene.

Mixtures of two or more olefins can also be polymerized. In contrast to some known iron and cobalt complexes, the transition metal complexes of the invention display a good polymerization activity even in the case of higher α-olefins, so that their suitability for copolymerization deserves particular emphasis. In particular, the transition metal complexes of the invention can be used for the polymerization or copolymerization of ethene or propene. As comonomers in the polymerization of ethene, preference is given to using $C_3$-$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at temperatures in the range from −60 to 350° C. under pressures of from 0.5 to 4000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. in the case of low-pressure polymerization processes, a temperature which is at least a few degrees below the softening temperature of the polymer is generally set. In particular, temperatures of from 50 to 180° C., preferably from 70 to 120° C., are set in these polymerization processes. In the case of suspension polymerizations, the polymerization is usually carried out in a suspension medium, preferably in an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242, 150 and U.S. Pat. No. 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or super-condensed mode, in which part of the circulating gas is cooled to below the dew point and is recirculated as a two-phase mixture to the reactor. It is also possible to using a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The monocyclopentadienyl complexes of the invention and the catalyst systems in which they are present can also be prepared by means of combinations of methods or their polymerization activity can be tested with the aid of these combined methods.

The process of the invention allows polymers of olefins to be prepared. The term "polymerization" as used here in the description of the present invention encompasses both polymerization and oligomerization, e.g. oligomers and polymers having molar masses $M_w$ in the range from about 56 to 10 000 000 can be produced by this process.

Owing to their good mechanical properties, the olefin polymers prepared using the catalyst system of the invention are particularly useful for the production of films, fibers and moldings.

EXAMPLES

All syntheses and polymerizations were carried out under a protective nitrogen atmosphere.

The density [g/cm$^3$] was determined in accordance with ISO 1183.

The Staudinger index ($\eta$)[dl/g] was determined using an automatic Ubbelohde viscometer (Lauda PVS 1) in decalin as solvent at 130° C. (ISO1628 at 130° C., 0.001 g/ml of decalin).

The NMR spectra were measured on a Bruker DRX 200 ($^1$H, 200.13 MHz). In $^1$H-NMR spectra, the signal of the incompletely deuterated part of the solvent used served as internal standard. All signals were calibrated to the appropriate literature values.

Mass spectra were recorded on a Finnigan MAT 8230, and high-resolution mass spectra were measured on a Micromass CTD ZAB-2F VH spectrometer.

Abbreviations in the Tables Below:
Cat. catalyst.
t(poly) polymerization time
Polymer amount of polymer formed Density polymer density
Prod. productivity of the catalyst system in g of polymer obtained per mmol of catalyst (chromium complex) used per hour Hexene whether or not hexene is present during the polymerization Example 1

1.1. Preparation of 2,3,4-trimethyl-1-(8-quinolyl)cyclopentadiene

A solution of 8.3 g (40 mmol) of 8-bromoquinoline in 100 ml of tetrahydrofuran was cooled to −80° C. and 16 ml of n-butyllithium (2.5 M in hexane, 40 mmol) were subsequently added dropwise. After the addition was complete, the mixture was stirred for a further 15 minutes at −80° C. and 4.96 g (40 mmol) of 2,3,4-trimethylcyclopent-2-enone were then added. The mixture was allowed to come to room temperature and was then refluxed for 30 minutes. After cooling to room temperature, the reaction mixture was admixed with ice water and 10 ml of concentrated hydrochloric acid and stirred for 30 minutes. A dilute aqueous ammonia solution was then added until a pH of 12 had been reached. The aqueous phase was then separated off from the organic phase and the aqueous phase was extracted twice with diethyl ether. The organic phases were combined, dried over magnesium sulfate, filtered and the solvent was distilled off. Distillation at 117-132° C. and 2×10$^{-2}$ mbar gave 4.02 g (17.1 mmol, 43%) of 2,3,4-trimethyl-1-(8-quinolyl)cyclopentadiene.

NMR $^1$H (200, 13 MHZ, CDCl$_3$): 1.81 (3H, s, Me); 1.82 (3H, s, Me); 1.94 (3H, s, Me); 3.48 (2H, s, CH$_2$); 7.26 (1H, dd); 7.43 (2H, m); 7.61 (1H, dd); 8.05 (1H, dd), 8.82 (1H, dd).

NMR $^1$H (50, 1 MHZ, CDCl$_3$): 11.6 (Me); 13.3 (Me); 13.9 (Me); 49.4 (CH$_2$); 121, 126.3, 126.4, 130.2, 136.4, 149.8 (CH$_{quinolyl+Cp}$); 129, 135.3, 136.8, 136.9, 138.3, 141.3, 147.4 (C$_{quinolyl+Cp}$).

1.2. Preparation of 3,4,5-trimethyl-1-(8-quinolyl)-2-trimethylsilylcyclopentadiene A solution of 0.87 g (3.7 mmol) of 2,3,4-trimethyl-1-(8-quinolyl)cyclopentadiene in 20 ml of tetrahydrofuran was added to a suspension of 0.15 g (3.7 mmol) of potassium hydride in 30 ml of tetrahydrofuran and the mixture was subsequently stirred at room temperature for 6 hours. 0.402 g (3.7 mmol) of trimethylsilyl chloride was added while stirring and the mixture was stirred at room temperature for a further 12 hours. The volatile constituents were distilled off and the residue obtained in this way was distilled. At 126-136° C. and 2×10$^{-2}$ mbar, 3,4,5-trimethyl-1-(8-quinolyl)-2-trimethylsilylcyclopentadiene distilled over in a yield of 0.455 g (1.5 mmol, 40%).

NMR $^1$H (200, 13 MHZ, CDCl$_3$): −0.51 (9H, s, SiMe$_3$); 1.89 (3H, s, Me); 1.97 (3H, s, Me); 2.04 (3H, s, Me); 4.47 (1H, s, Cp); 7.25 (1H, dd, H$^3$); 7.42-7.46 (2H, m, H$^5$ u. H$^7$); 8.03 (1H, dd, H$^4$); 8.83 (1H, dd, H$^2$).

MS (EI), m/e (%): 307 (26) [M$^+$]; 292 (70) [M$^+$-CH$_3$]; 234 (100) (M+—Si(CH$_3$)$_3$—CH$_3$).

1.3. Preparation of (3,4,5-trimethyl-1-(8-quinolyl)-2-trimethylsilylcyclopentadienyl)chromium dichloride

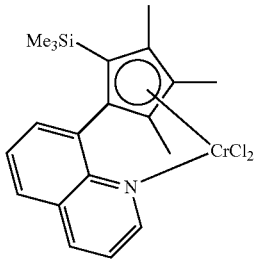

A solution of 0.124 g (0.4 mmol) of 3,4,5-trimethyl-1-(8-quinolyl)-2-trimethylsilylcyclopentadiene in 20 ml of tetrahydrofuran was added to a suspension of 0.016 g (0.4 mmol) of potassium hydride in 20 ml of tetrahydrofuran. After the addition was complete, the reaction mixture was stirred at room temperature for 6 hours and subsequently added to a solution of 0.15 g (0.4 mmol) of chromium trichloride tris(tetrahydrofuran) in 20 ml of tetrahydrofuran while stirring. The mixture was stirred for a further 12 hours at room temperature, and the solvent was then distilled off and the residue was washed 3 times with hexane. The soluble components of the residue obtained in this way were taken up in hot toluene and filtered. The filtrate was freed of solvent, washed and dried under reduced pressure. This gave 0.11 g (0.26 mmol) of (3,4,5-trimethyl-1-(8-quinolyl)-2-trimethylsilylcyclopentadienyl)chromium dichloride (65%).

NMR $^1$H (200, 13 MHZ, CDCl$_3$): −75 (1H, H$^2$); −56.9 (1H, H$^4$); −36.7 (3H, Me$^{9+10}$); −27.3 (3H, Me$^{9+10}$); −16.7 (1H, Hs); 12.2 (3H, Me$^{11}$); 15.7 (1H, Hs); 51.1 (1H, H$^3$).

MS (EI), m/e (%): 428 (84) [M$^+$]; 392 (100) [M$^+$-HCl]; 356 (9) [M$^+$-2HCl].

1.4. Reaction of (3,4,5-trimethyl-1-(8-quinolyl)-2-trimethylsilylcyclopentadienyl)chromium dichloride with BBr$_3$ to form (3,4,5-trimethyl-1-(8-quinolyl)-2-bromodimethylsilylcyclopentadienyl)-chromium dibromide 1.13 g (4.5 mmol) of boron tribromide were added to a solution of 0.276 g (0.64 mmol) of (3,4,5-trimethyl-1-(8-quinolyl)-2-trimethylsilylcyclopentadienyl)chromium dichloride in 25 ml of dichloromethane. After the addition was complete, the reaction mixture was stirred at 70° C. for 2 days and the solvent was subsequently distilled off and the residue was washed twice with hexane. The soluble components of the residue obtained in this way were taken up in toluene and filtered. The filtrate was freed of solvent, washed with hexane and dried under reduced pressure. This gave 0.144 g (0.25 mmol) of (3,4,5-trimethyl-1-(8-quinolyl)-2-bromodimethylsilylcyclopentadienyl)chromium dibromide (39%).

MS (EI), m/e (%): 680 (21) [M$^+$]; 501 (100) [M$^+$-Br]; 290 (69) [M$^+$-2Br—HBr—Cr].

The invention claimed is:

1. A cyclopentadienyl complex of group 6 comprising at least one silyl group, wherein the silyl group comprises at least one halogen substituent the cyclopentadienyl complex is a monocyclopentadienyl complex comprising a formula of Cp-R$^{15A}_v$-A$^{1A}$-M$^{1A}$-X$^A_t$, wherein Cp-R$^{15A}_v$-A$^{1A}$ is

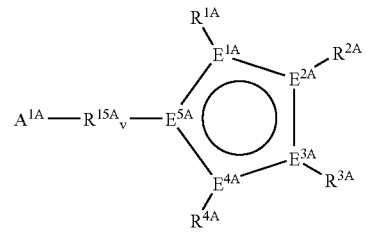

(IV)

E$^{1A}$-E$^{5A}$ are carbon;

R$^{1A}$-R$^{4A}$ are each, independently of one another, hydrogen, C$_1$-C$_{22}$-alkyl, C$_2$-C$_{22}$-alkenyl, C$_6$-C$_{22}$-aryl, and arylalkyl comprising from 1 to 10 carbon atoms in the alkyl part and 6-20 carbon atoms in the aryl part, wherein radicals R$^{1A}$-R$^{4A}$ can be substituted by at least one halogen, and/or two vicinal radicals R$^{1A}$-R$^{4A}$ can be joined to form a five-, six- or seven-membered ring, and/or two vicinal radicals R$^{1A}$-R$^{4A}$ can be joined to form a five-, six- or seven-membered heterocycle comprising at least one atom from the group consisting of N, P, O and S, with the proviso that at least one R$^{1A}$-R$^{4A}$ is SiR$_2$D;

D is fluorine, chlorine, bromine or iodine;

R are each, independently of one another, hydrogen C$_1$-C$_{22}$-alkyl, C$_2$-C$_{22}$-alkenyl, C$_6$-C$_{22}$-aryl, and arylalkyl comprising from 1 to 16 carbon atoms in the alkyl part and from 6 to 21 carbon atoms in the aryl part, wherein radicals R can be substituted by at least one halogen, and/or two radicals R can be joined to form a five-, six- or seven-membered ring;

R$^{15A}$ is a divalent bridge between A$^{1A}$ and Cp selected tram the group consisting at

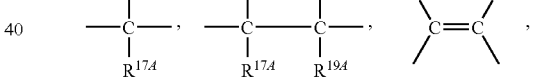

R$^{16A}$-R$^{19A}$ are each, independently of one another, hydrogen, C$_1$-C$_{20}$-alkyl, C$_2$-C$_{20}$-alkenyl, C$_6$-C$_{20}$-aryl, and arylalkyl comprising from 1 to 10 carbon atoms in the alkyl part and 6-20 carbon atoms in the aryl part, wherein radicals R$^{16A}$-R$^{19A}$ can be substituted by at least one halogen, and/or two geminal or vicinal radicals R$^{16A}$-R$^{19A}$ can be joined to form a five- or six-membered ring;

A$^{1A}$ in an uncharged donor group —NR$^{23A}$— or —NR$^{22A}_2$;

R$^{22A}$ are each, independently of one another, C$_1$-C$_{10}$-alkyl, C$_2$-C$_{22}$-alkenyl, C$_6$ C$_{22}$-aryl, and arylalkyl comprising from 1 to 10 carbon atoms in the alkyl part and from 6 to 20 carbon atoms in the aryl part, wherein radicals R$^{22A}$ can be substituted by at least one halogen and/or two radicals R$^{22A}$ can be joined to form a five, six- or seven-membered ring;

M$^{1A}$ is a metal selected from the group consisting of chromium, molybdenum, and tungsten, X$^A$ is fluorine, chlorine, bromine, or iodine;

t is 1 or 2, with the proviso that the cyclopentadienyl complex is uncharged; and v is 0 or 1.

2. The cyclopentadienyl complex according to claim 1, wherein D is chlorine or bromine.

3. The cyclopentadienyl complex according to claim 1, wherein R is $C_1$-$C_{22}$-alkyl.

4. A catalyst system for olefin polymerization comprising:
A) at least one cyclopentadienyl complex of group 6 comprising at least one silyl group, wherein the silyl group comprises at least one halogen substituent, the cyclopentadienyl complex is a monocyclopentadienyl complex comprising a formula Cp-$R^{15A}_v$-$A^{1A}$-$M^{1A}$-$X^A_t$, wherein Cp-$R^{15A}_v$-$A^{1A}$ is

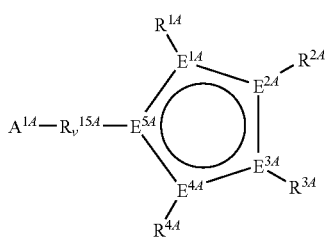
(IV)

$E^{1A}$-$E^{5A}$ are carbon;
$R^{1A}$-$R^{4A}$ are each, independently of one another, hydrogen, $C_1$-$C_{22}$-alkyl, $C_2$-$C_{22}$-alkenyl, $C_6$-$C_{22}$-aryl, and arylalkyl comprising from 1 to 10 carbon atoms in the alkyl part and 6-20 carbon atoms in the aryl part, wherein radicals $R^{1A}$-$R^{4A}$ can be substituted by at least one halogen, and/or two vicinal radicals $R^{1A}$-$R^{4A}$ can be joined to form a five-, six- or seven-membered ring, and/or two vicinal radicals $R^{1A}$-$R^{4A}$ can be joined to form a five-, six- or seven-membered heterocycle comprising at least one atom from the group consisting of N, P, O and S, with the proviso that at least one $R^{1A}$-$R^{4A}$ is $SiR_2D$;
D is fluorine, chlorine, bromine or iodine;
R are each, independently of one another, hydrogen, $C_1$-$C_{22}$alkyl, $C_2$-$C_{22}$-alkenyl, $C_6$-$C_{22}$, and arylalkyl comprising from 1 to 16 carbon atoms in the alkyl part and from 6 to 21 carbon atoms in the aryl part, wherein radicals R can be substituted by at least one halogen, and/or two radicals R can be joined to form a five-, six- or seven-membered ring;
$R^{15A}$ is a divalent bridge between $A^{1A}$, and Cp selected from the group consisting of

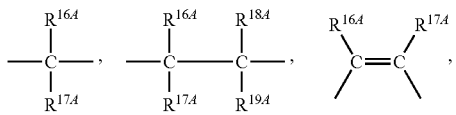

$R^{16A}$-$R^{19A}$ are each, independently of one another, hydrogen, $C_1$-$C_{20}$-alkyl, $C_2$-$C_{20}$-alkenyl, $C_6$-$C_{20}$-aryl, and arylalkyl comprising from 1 to 10 carbon atoms in the alkyl part and 6-20 carbon atoms in the aryl part, wherein radicals $R^{16A}$-$R^{19A}$ can be substituted by at least one halogen, and/or two geminal or vicinal radicals $R^{16A}$-$R^{19A}$ can be joined to form a five- or six-membered ring;
$A^{1A}$ is an uncharged donor group —$NR^{22A}$— or —$NR^{22A}_2$;
$R^{22A}$ are each, independently of one another, $C_1$-$C_{10}$-alkyl, $C_2$-$C_{22}$-alkenyl, $C_1$-$C_{22}$-aryl, and arylalkyl comprising from 1 to 10 carbon atoms in the alkyl part and from 6 to 20 carbon atoms in the aryl part, wherein radicals $R^{22A}$ can be substituted by at least one halogen and/or two radicals $R^{22}A$ can be joined to form a five-, six- or seven-membered ring;
$M^{1A}$ is a metal selected from the group consisting of chromium, molybdenum, and tungsten,
$X^A$ is fluorine, chlorine, bromine, or iodine;
t is 1 or 2, with the proviso that the cyclopentadienyl complex is uncharged; and
v is 0 or 1;
B) optionally, an organic or inorganic support;
C) optionally, at least one activating compound,
D) optionally, at least one additional catalyst suitable for olefin polymerization; and
E) optionally, at least one metal compound comprising a metal of group 1, 2 or 13 of the Periodic Table.

5. A process for preparing at least one polyolefin by polymerizing or copolymerizing at least one olefin in presence of a catalyst system according to claim 4.

6. A process for preparing a cyclopentadienyl complex of group 6 comprising at least one cyclopentadienyl system substituted by at least one silyl group, wherein the silyl group comprises at least one halogen substituent, wherein the cyclopentadienyl complex is a monocyclopentadienyl complex comprising formula Cp-$R^{15A}_v$-$A^{1A}$-$M^{1A}$-$X^A_t$, wherein Cp-$R^{15A}_v$-$A^{1A}$ is

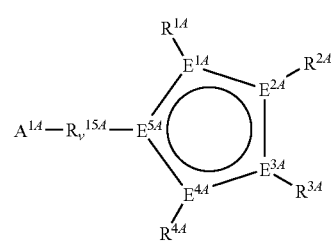
(IV)

$E^{1A}$-$E^{5A}$ are carbon;
$R^{1A}$-$R^{4A}$ are each, independently of one another, hydrogen, $C_1$-$C_{22}$-alkyl, $C_2$-$C_{22}$-alkenyl, $C_6$-$C_{22}$-aryl, and arylalkyl comprising from 1 to 10 carbon atoms in the alkyl part and 6-20 carbon atoms in the aryl part, wherein radicals $R^{1A}$-$R^{4A}$ can be substituted by at least one halogen, and/or two vicinal radicals $R^{1A}$-$R^{4A}$ can be joined to form a five-, six- or seven-membered ring, and/or two vicinal radicals $R^{1A}$-$R^{4A}$ can be joined to form a five-, six- or seven-membered heterocycle comprising at least one atom from the group consisting of N, P, O and S, with the proviso that at leant one $R^{1A}$-$R^{4A}$ is $SiR_2D$;
D is fluorine, chlorine, bromine or iodine;
R are each, independently of one another, hydrogen, $C_1$-$C_{22}$-alkyl, $C_2$-$C_{22}$alkenyl, $C_6$-$C_{22}$-aryl, and arylalkyl comprising from 1 to 16 carbon atom in the alkyl part and from 6 to 21 carbon atoms in the aryl part, wherein radicals R can be substituted by at least one halogen, and/or two radicals R can be joined to form a five-, six- or seven-membered ring:
$R^{15A}$ is a divalent bridge between $A^{1A}$, and Cp selected from the group consisting of

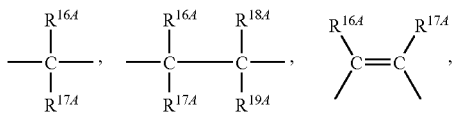

$R^{16A}$-$R^{19A}$ are each, independently of one another, hydrogen, $C_1$-$C_{20}$-alkyl, $C_2$-$C_{20}$-alkenyl, $C_6$-$C_{20}$-aryl, and arylalkyl comprising from 1 to 10 carbon atoms in the alkyl part and 6-20 carbon atoms in the aryl part, wherein radicals $R^{16A}$-$R^{19A}$ can be substituted by at least one halogen, and/or two geminal or vicinal radicals $R^{16A}$-$R^{19A}$ can be joined to form a five- or six-membered ring;

$A^{1A}$ is an uncharged donor group —$NR^{22A}$— or —$NR^{22A}_2$ system;

$R^{22A}$ are each, independently of one another, $C_1$-$C_{10}$-alkyl, $C_2$-$C_{22}$-alkenyl, $C_6$-$C_{22}$-aryl, and arylalkyl comprising from 1 to 10 carbon atoms in the alkyl part and from 6 to 20 carbon atoms in the aryl part, wherein radicals $R^{22A}$ can be substituted by at least one halogen and/or two radicals $R^{22A}$ can be joined to form a five-, six- or seven-membered ring;

$M^{1A}$ is a metal selected from the group consisting of chromium, molybdenum, and tungsten;

$X^A$ is fluorine, chlorine, bromine, or iodine;

t is 1 or 2, with the proviso that the cyclopentadienyl complex is uncharged; and v is C or 1;

wherein the process comprises:

reacting the cyclopentadienyl complex of group 6 comprising at least one cyclopentadienyl system with a boron trihalide.

7. The process of claim 6, wherein the boron trihalide is $BD_3$, wherein D is fluorine, chlorine, bromine, or iodine.

8. The process of claim 7, wherein D is chlorine or bromine.

* * * * *